United States Patent
Costanzo et al.

[11] Patent Number: 6,069,254
[45] Date of Patent: *May 30, 2000

[54] CARBOXAMIDE DERIVATIVES OF PIPERIDINE FOR THE TREATMENT OF THROMBOSIS DISORDERS

[75] Inventors: Michael J. Costanzo, Ivyland; William J. Hoekstra, Villanova; Bruce E. Maryanoff, Forest Grove, all of Pa.

[73] Assignee: Ortho Pharmaceutical Corp., Raritan, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/841,016

[22] Filed: Apr. 29, 1997

Related U.S. Application Data
[60] Provisional application No. 60/016,675, May 1, 1996.

[51] Int. Cl.$^7$ ...................... C07D 401/12; C07D 401/14; C07D 403/14; A61K 31/445

[52] U.S. Cl. .......................... 546/189; 546/176; 546/187; 514/314; 514/316

[58] Field of Search ...................................... 546/193, 198, 546/208, 212, 187, 189, 176; 514/316, 318, 323, 324, 314

[56] References Cited

U.S. PATENT DOCUMENTS
5,639,765  6/1997  Ruminski .................................. 514/329

OTHER PUBLICATIONS
Hoekstra et al., Bioorganic & Medicinal Chemistry Letters, 6(20)pp. –2371–2376, Pergamon Press Oct. 20, 1996.
Costa, B.R. et al, J. Med. Chem., 1994, 37(2), pp. 314–321, online search results relied upon.

*Primary Examiner*—Alan L. Rotman
*Attorney, Agent, or Firm*—Ralph R. Palo

[57] ABSTRACT

Carboxamide derivatives of pyrrolidine, piperidine, and hexahydroazepine of formula (I):

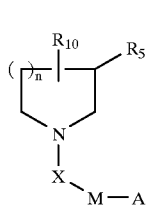

are disclosed as useful in treating platelet-mediated thrombotic disorders.

2 Claims, No Drawings

CARBOXAMIDE DERIVATIVES OF PIPERIDINE FOR THE TREATMENT OF THROMBOSIS DISORDERS

This application claims benefit of Provisional Application number 60/016,675, filed May 1, 1996.

BACKGROUND OF THE INVENTION

Platelet aggregation constitutes the initial hemostatic response to curtail bleeding induced by vascular injury. However, pathological extension of this normal hemostatic process can lead to thrombus formation. The final, common pathway in platelet aggregation is the binding of fibrinogen to activated, exposed platelet glycoprotein IIb/IIIa (GPIIb/IIIa). Agents which interrupt binding of fibrinogen-to GPIIb/IIIa, therefore, inhibit platelet aggregation. These agents are, therefore, useful in treating platelet-mediated thrombotic disorders such as arterial and venous thrombosis, acute myocardial infarction, unstable angina, reocclusion following thrombolytic therapy and angioplasty, inflammation, and a variety of vaso-occlusive disorders. The fibrinogen receptor (GPIIb/IIIa) is activated by stimuli such as ADP, collagen, and thrombin exposing binding domains to two different peptide regions of fibrinogen: α-chain Arg-Gly-Asp (RGD) and γ-chain His-His-Leu-Gly-Gly-Ala-Lys-Gln-Ala-Gly-Asp-Val (HHLGGAKQAGDV, γ400–411). Since these peptide fragments themselves have been shown to inhibit fibrinogen binding to GPIIb/IIIa, a mimetic of these fragments would also serve as an antagonist. In fact, prior to this invention, potent RGD-based antagonists have been revealed which inhibit both fibrinogen binding to GPIIb/IIIa and platelet aggregation e.g., Ro-438857 (L. Alig, *J. Med. Chem.* 1992, 35, 4393) has an $IC_{50}$ of 0.094 μM against in vitro thrombin-induced platelet aggregation. Some of these agents have also shown in vivo efficacy as antithrombotic agents and, in some cases, have been used in conjunction with fibrinolytic therapy e.g., t-PA or streptokinase, as well (J. A. Zablocki, *Current Pharmaceutical Design* 1995, 1, 533). As demonstrated by the results of the pharmacological studies described hereinafter, the compounds of the present invention show the ability to block fibrinogen binding to isolated GPIIb/IIIa ($IC_{50}$'s 0.0002–1.39 μM), inhibit platelet aggregation in vitro in the presence of a variety of platelet stimuli (0.019–65.0 μM vs. thrombin), and furthermore, inhibit ex vivo platelet aggregation in animal models. Additionally, these agents exhibit efficacy in animal thrombosis models as their progenitors had shown ("Nipecotic Acid Derivatives As Antithrombotic Compounds," application Ser. No. 08/213,772, filed Mar. 16, 1994). The compounds of the present invention show efficacy as antithrombotic agents by virtue of their ability to prevent platelet aggregation. Additionally, because the compounds of this invention inhibit integrin-mediated cell-cell or cell-matrix adhesion, they may also be useful against inflammation, bone resorption, tumor cell metastasis, etc. (D. Cox, *Drug News&Perspectives* 1995, 8, 197).

DISCLOSURE OF THE INVENTION

The present invention is directed to compounds represented by the following general formula (I):

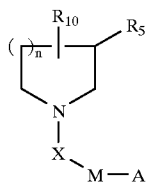

wherein A, X, M, $R_5$, $R_{10}$, and n are as hereinafter defined. These platelet aggregation inhibitors are useful in treating platelet-mediated thrombotic disorders such as arterial and venous thrombosis, acute myocardial infarction, reocclusion following thrombolytic therapy and angioplasty, inflammation, unstable angina, and a variety of vaso-occlusive disorders. These compounds are also useful as antithrombotics used in conjunction with fibrinolytic therapy (e.g., t-PA or streptokinase). Pharmaceutical compositions containing such compounds are also part of the present invention.

DETAILED DESCRIPTION OF THE INVENTION

More particularly, the present invention is directed to compounds of the following formula (I):

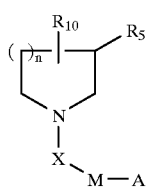

wherein M is $(CH_2)_m$ or piperidin-1-yl;

wherein A is selected from any of piperidin-2-yl, piperidin-3-yl, piperidin-4-yl, piperazin-1-yl, pyrrolidin-2-yl, pyrrolidin-3-yl, $NHR^2$, or

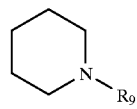

wherein $R_9$ is selected from any of H, alkyl, CH(NH), CMe(NH) or acyl, preferably $R_9$ is hydrogen;

wherein $R_{10}$ is H or $C(O)N(R^1)YZ$ wherein $R_1$ is selected from H or cycloalkyl;

wherein $R^2$ is selected from any of H, alkyl or acyl. Preferably, $R^2$ is hydrogen;

wherein $R_5$ is H or $C(O)NHQ(CHW)_rCO_2R_8$; wherein Q is selected from $CH_2$, CH-aryl, CH-heteroaryl, CH-substituted-heteroaryl or CH-alkyl; preferably Q is $CH_2$, CH-substituted-heteroaryl or CH-heteroaryl; W is selected from H or $N(R_6)T$-$R_7$, preferably W is H when Q is CH, and $N(R_6)$-T-$R_7$ when Q is $CH_2$; wherein $R_6$ is selected from any of H, alkyl or acyl; preferably $R_6$ is hydrogen, T is selected fron C(O), C(N—CN) or $SO_2$, preferably T is C(O) and $R_7$ is selected from any of alkyl, aryl, aralkyl, alkoxy, or aminoalkyl; and $R_8$ is selected from H, alkyl or aralkyl; preferably $R_8$ is H.

wherein m is the integer 1, 2, or 3. Preferably m is 1 or 2;

wherein X is selected from any of C(O), C(O)O, C(O)NH, CH$_2$, or SO$_2$;

wherein n is the integer 1, 2, or 3;

wherein r is 0 or 1;

wherein Y is selected from any of (CH$_2$)$_p$, CH(R$^3$)(CH$_2$)$_q$, (CH$_2$)$_q$CH(R$^3$), (CH(COR$^4$)CH$_2$)$_q$, (CH$_2$)$_q$CHOH or piperidine-3-carboxylic acid; with the proviso that when Y is (CH$_2$)$_p$ and p is 2, X is other than C(O) or when X is C(O) then either R$^1$ is other than H or R$^2$ is other than H, and with the proviso that when Y is (CH(CO$_2$R$^4$)CH$_2$)$_q$ X is other than C(O) or CH$_2$;

wherein p is 2 or 3;

wherein q is 1, 2, or 3. Preferably, q is 1.

wherein R$^3$ is alkyl, C$_2$–C$_8$ alkenyl, C$_2$–C$_8$ alkynyl, aryl, aralkyl or heteroaryl;

wherein R$^4$ is H or alkyl or cycloalkyl. Preferably, R$^4$ is hydrogen.

wherein Z is CO$_2$H, CO$_2$alkyl, SO$_3$H, PO$_3$H$_2$, or 5-tetrazole; provided that at least one of R$_5$ and R$_{10}$ is hydrogen;

or the enantiomer or the pharmaceutically acceptable salt thereof.

Preferably, the group C(O)N(R$^1$)YZ is attached to the ring carbon of the central azacycle at the 3- or 4-position (4-position when larger than a five-membered ring), and most preferably the 3-position.

As used herein, unless otherwise noted alkyl and alkoxy whether used alone or as part of a substituent group, include straight and branched chains having 1–8 carbons. For example, alkyl radicals include methyl, ethyl, propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 5–8 ring carbons and preferably 6–7 carbons.

The term "aryl", "heteroaryl" or "substituted heteroaryl" as used herein alone or in combination with other terms indicates aromatic or heteroaromatic groups such as phenyl, naphthyl, pyridyl, thienyl, furanyl, or quinolinyl wherein the substituent is an alkyl group. The term "aralkyl" means an alkyl group substituted with an aryl group.

The term "acyl" as used herein means an organic radical having 2–6 carbon atoms derived from an organic acid by removal of the hydroxyl group.

The compounds of the present invention may also be present in the form of a pharmaceutically acceptable salt. The pharmaceutically acceptable salt generally takes a form in which the nitrogen on the 1-piperidine (pyrrolidine, piperazine) substituent is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic.

Particularly preferred compounds of the present invention include those compounds shown in Table 1, where "Subst" indicates the position of attachment of the group C(O)N(R$^1$)YCO$_2$H to the central azacycle and where the letter "R" after the numeral "3" indicates the absolute configuration (Cahn-Ingold-Prelog rules). Those numerals not having any configuration specified are racemic mixtures.

TABLE I

| # | Subst | m | n | X | R$^1$ | R$^2$ | Y | Z |
|---|---|---|---|---|---|---|---|---|
| 1 | 3 | 2 | 2 | C(O) | H | H | CH(Ph)CH$_2$ | CH |
| 2 | 3 | 1 | 2 | NHCO | H | H | CH$_2$CHMe | CH |
| 3 | 3 | 1 | 2 | OC(O) | H | H | (R)—CH(CO2Me)CH$_2$ | CH |
| 4 | 3 | 2 | 1 | C(O) | H | H | CH(4-Me—Ph)CH$_2$ | CH |
| 5 | 4 | 2 | 2 | C(O) | H | H | CH(Me)CH$_2$ | CH |
| 6 | 4 | 2 | 2 | C(O) | H | H | CH(4-CO$_2$H—Ph)CH$_2$ | CH |
| 7 | 3 | 2 | 2 | C(O) | H | Me | CH$_2$CH$_2$ | CH |
| 8 | See structure | | | | | | | |
| 9 | 3 | 2 | 2 | C(O) | H | H | CH(Me$_3$Si-ethynyl)CH$_2$ | CH |
| 10 | See structure | | | | | | | |
| 11 | 3R | 2 | 2 | CO | H | H | CH$_2$CH(OH) | CH |
| 12 | 3 | 2 | 2 | SO$_2$ | H | H | CH$_2$CH$_2$ | CH |
| 13 | See structure | | | | | | | |
| 14 | 3 | 2 | 2 | CO | H | Me | CH(3,4-CCH$_2$O—Ph)CH$_2$ | N |
| 15 | 3 | 2 | 2 | CO | H | Me | CH(3quinolinyl)CH$_2$ | N |
| 16 | 3R | 2 | 2 | CO | H | H | S-CH(3,4-OCH$_2$O—Ph)CH$_2$ | CH |
| 17 | 3 | 2 | 3 | CO | H | H | CH(3-quinolinyl)CH$_2$ | CH |
| 18 | 3R | 2 | 2 | CO | H | H | S-CH(3-quinolinyl)CH$_2$ | CH |
| 19 | 3R | 2 | 2 | CO | H | H | S-CH(t-butylethynyl)CH$_2$ | CH |

TABLE I-continued
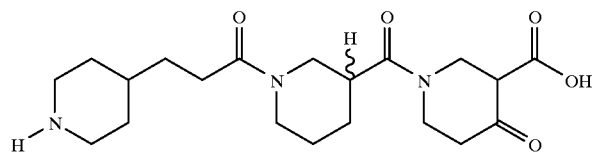
| # | Subst | m | n | X | R¹ | R² | Y | Z |
|---|-------|---|---|-----|----|----|--------------------------|-----|
| 20 | 3 | 2 | 2 | CH₂ | H | H | S-CH(3,4-OCH₂O—Ph)CH₂ | CH |
| 21 | 3R | 2 | 2 | CO | H | H | S-CH(3-pyridyl)CH₂ | CH |
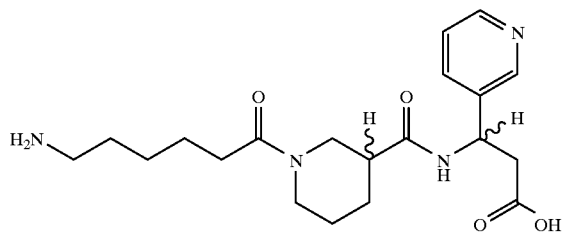
8
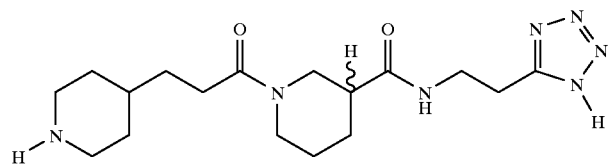
10
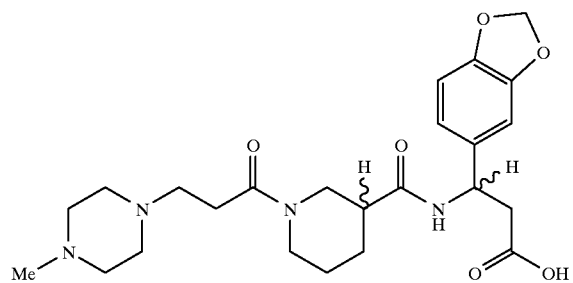
13
14

TABLE I-continued

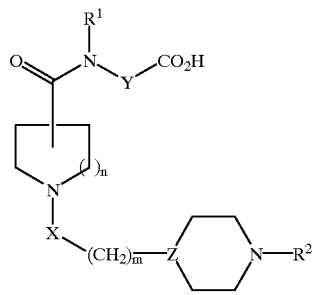

| # | Subst | m | n | X | R¹ | R² | Y | Z |
|---|---|---|---|---|---|---|---|---|
| 16 | | | | | | | | |

The compounds of the invention wherein $R_5$ is H, $R_{10}$ is $C(O)N(R^1)YZ$, M is $(CH_2)m$ and A is piperidin-2-yl, piperidin-3-yl, piperidin-4-yl, piperazin-1-yl, pyrrolidin-2-yl, pyrrolidin-3-yl or $NHR^2$ may be prepared as shown in Scheme AA. In this scheme nipecotic acid allyl ester (either the racemic mixture or either separate enantiomer) may be treated with resin-bound 4-piperidinepropionic acid in the presence of DIC/HOBT and a tertiary amine. The allyl ester is then removed via palladium-mediated catalysis and the iterative coupling process continued to give final product upon saponification with potassium trimethylsilanolate (e.g., compound 1). By analogy, urea and urethane-based replacements for the tertiary amide (compounds 2 and 3) were prepared by reaction of solid-supported amine (alcohol) with p-nitrophenylchloroformate and then ethyl nipecotate (S. M. Hutchins, Tetrahedron Lett. 1994, 35, 4055).

Three-substituted 3-aminopropionic acid ester intermediates were prepared utilizing a modified Knoevenagel procedure (Scheme AG; E. Profft, J. Prakt. Chem. 1965, 30, 18) followed by Fischer esterification of the carboxylic acid product (when not commercially-available). These intermediates were prepared in enantiomerically-enriched form by penicillin amidase resolution of racemic phenylacetamides such as intermediate AG3 (V. A. Soloshonok, Tetrahedron: Asymmetry 1995, 6, 1601). Here, the undesired R-enantiomer is hydrolyzed by amidase while the desired S-enantiomer retains the phenylacetyl group. Resolutions may also be performed on the (−)-ephedrine salts of racemic three-substituted 3-N-Boc-aminopropionic acids as published (J. A. Zablocki, J. Med. Chem. 1995, 38, 2378). Ethyl nipecotate and ethyl isonipecotate are commercially-available intermediates.

Synthesis of 5- and 7-membered ring analogues of nipecotamides (4 and 17, respectively) were prepared by solid-phase synthesis using methyl pyrrolidine-3-carboxylate and methyl hexahydroazepine-3-carboxylate intermediates for the analogous conversion of AA2 to AA3 (Scheme AA). Methyl pyrrolidine-3-carboxylate and methyl hexahydroazepine-3-carboxylate were prepared as published (H. Rapoport, J. Org. Chem. 1974, 39, 893). For example, N-benzyl hexahydroazepin-2-one was reacted with lithium diisopropylamide/diethylcarbonate and this product then reduced with lithium aluminum hydride to afford N-benzyl-3-hydroxymethylhexahydroazepine. The benzyl group was removed by hydrogenolysis ($H_2$, Pd-C, MeOH), the nitrogen protected (di-t-butyldicarbonate/sodium hydroxide), and the alcohol oxidized with chromium trioxide to give N-Boc-hexahydroazepine-3-carboxylic acid. The Boc group was removed concomitant with carboxylate esterification using HCl/MeOH to afford methyl hexahydroazepine-3-carboxylate.

Piperazine analogs were prepared, as exemplified in Scheme AB, as published (S. G. Gilbreath, J. Am. Chem. Soc. 1988, 110, 6172). Tetrazoles (13) were prepared from the corresponding nitriles using azidotrimethylsilane/dibutyltin oxide as published (Scheme AC; S. J. Wittenberger, J. Org. Chem. 1993, 58, 4139). Here, the nitrile precursor AC2 was prepared by standard amide bond coupling with 3-aminopropionitrile, and reduced on the final synthetic step using platinum dioxide-mediated hydrogenation (W. J. Hoekstra, J. Med. Chem. 1995, 38, 1582).

N-Methylpiperidine analogues can be prepared by Fmoc-based solid-phase peptide synthesis techniques as shown in scheme AD (P. Sieber, Tetrahedron Lett. 1987, 28, 6147). The Fmoc protecting groups were cleaved by 20% piperidine/DMF, couplings were effected using DIC/HOBT/DMF, and final products were removed from the resin with 95% TFA.

Sulfonamide 12 was prepared as shown in Scheme AE. Intermediate AE1 was isolated in two steps from 4-pyridineethanesulfonic acid by hydrogenation/protection as described (J. I. DeGaw, J. Heterocyclic Chem. 1966, 3, 90), and then chlorinated using standard thionyl chloride conditions (P. J. Hearst, *Org. Syn.* 1950, 30, 58) to give AE2. Intermediate AE2 was then carried forward to final product using standard solution-phase synthesis (W. J. Hoekstra, *J. Med. Chem.* 1995, 38, 1582).

Piperidinepropyl-nipecotamide 20 was prepared as shown in Scheme AF. Ester AF1 was Boc-protected using standard Boc-ON conditions (D. S. Tarbell, *Proc. Natl. Acad. Sci. USA* 1972, 69, 730), and then reduced to its corresponding primary alcohol with DiBAL-H/THF (E. Winterfeldt, *Syn-thesis* 1975, 617) to give intermediate AF2. This compound was converted to its corresponding tosylate AF3 using p-TsCl (L. F. Awad, *Bull. Chem. Soc. Jpn.* 1986, 59, 1587). Ethyl nipecotate was then alkylated with intermediate AF3 using standard conditions (benzene/heat; I. Seki, *Chem. Pharm. Bull. Jpn.* 1970, 18, 1104).

Enantiomerically-enriched R-(−)-nipecotic acid ethyl ester was isolated by chiral resolution of racemic material as its corresponding D-tartaric acid salt (A. M. Akkerman, *Rec. Trav. Chim. Pays-Bas* 1951, 70, 899)

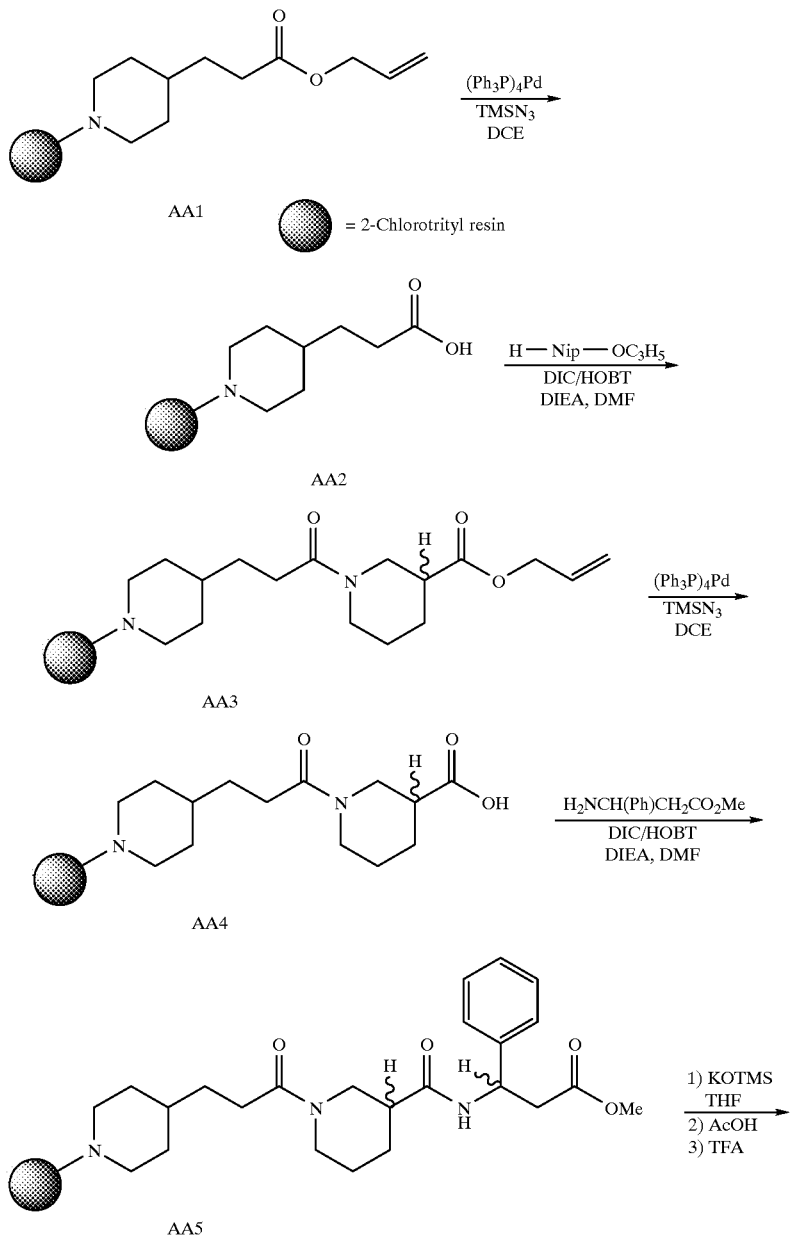

-continued
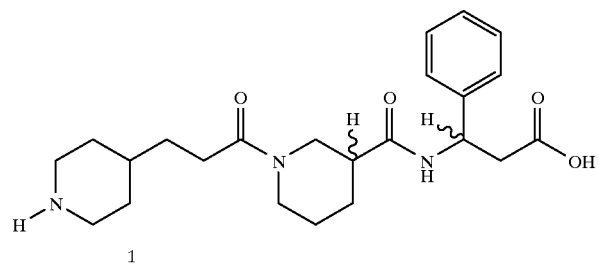
SCHEME AB
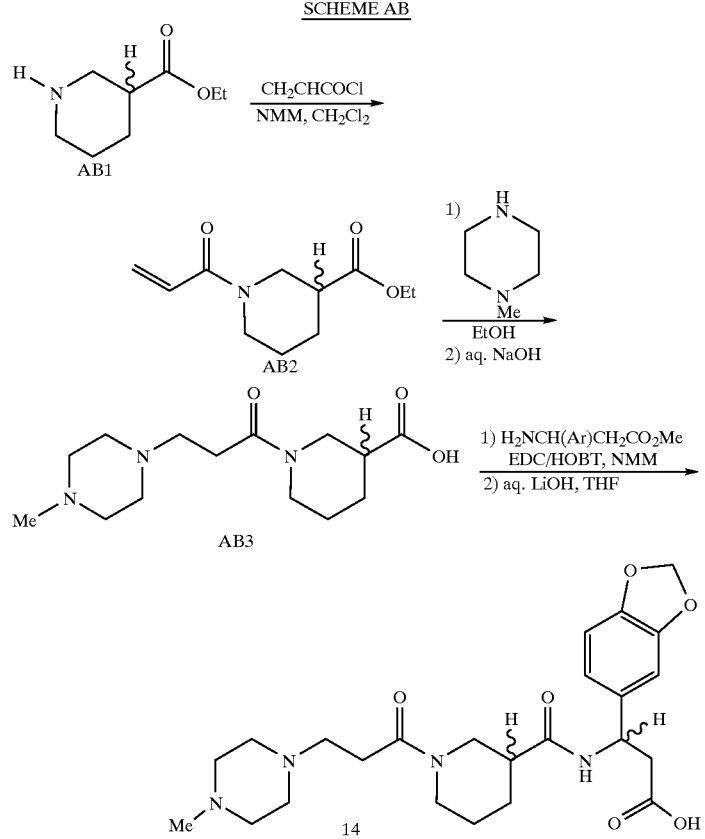
SCHEME AC
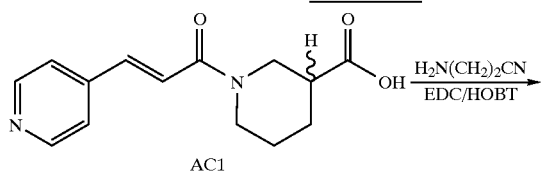

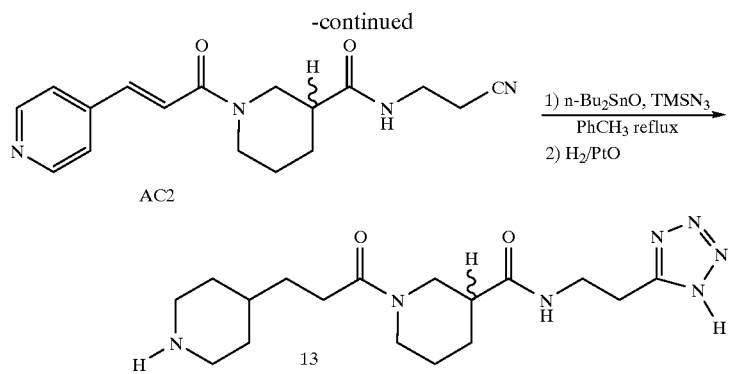
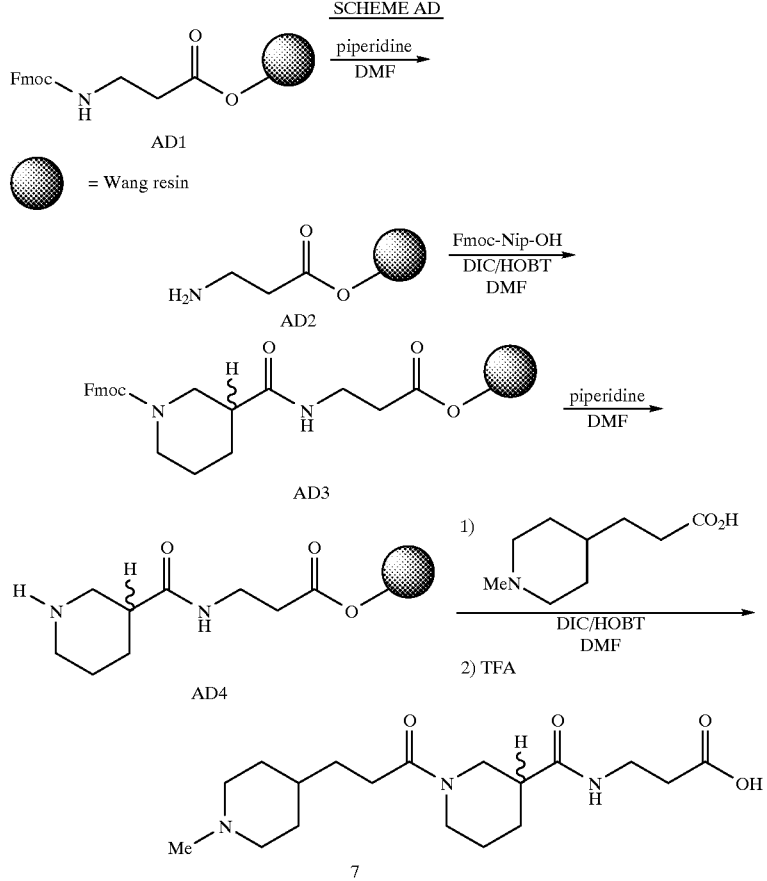
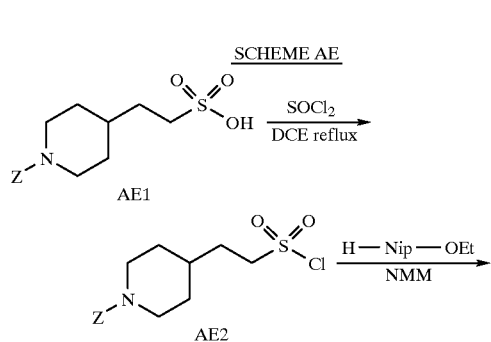
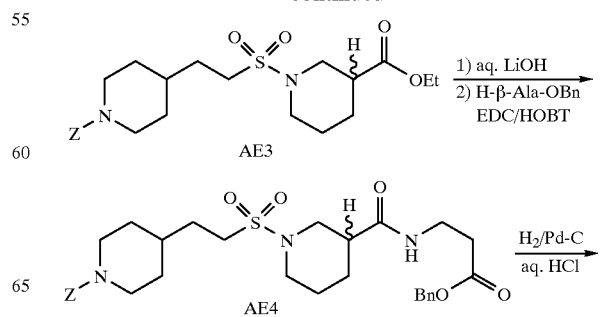

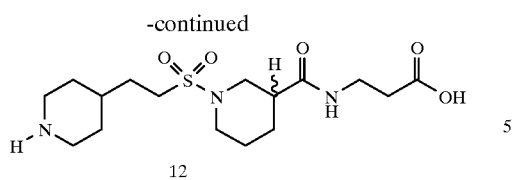
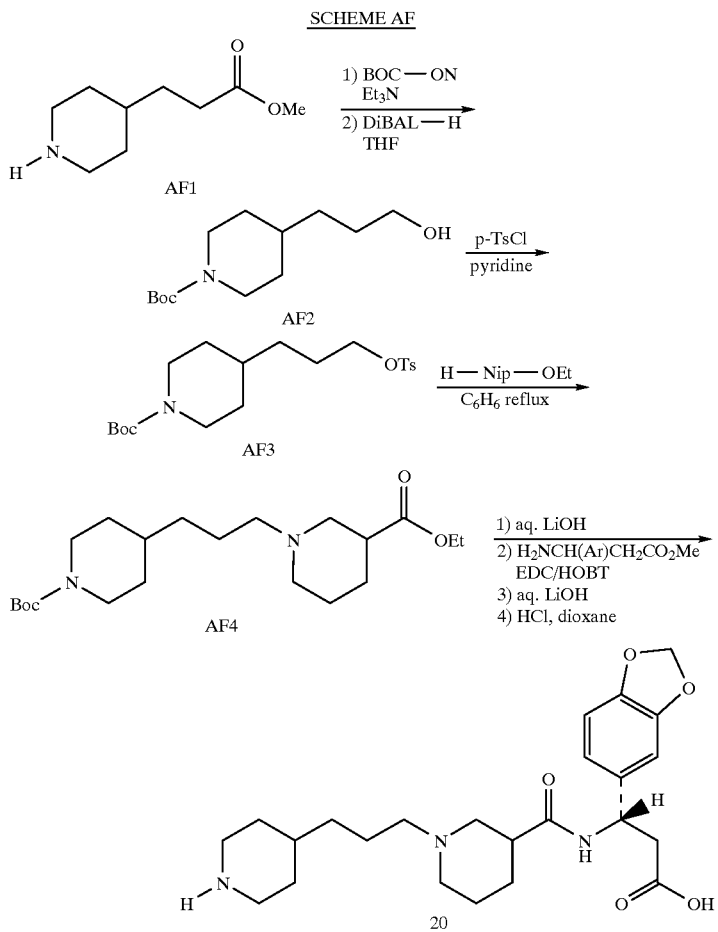
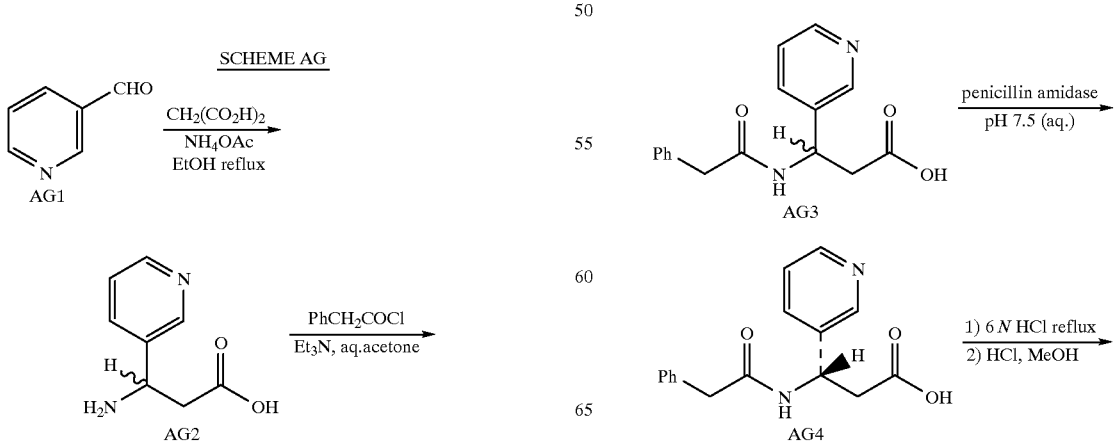

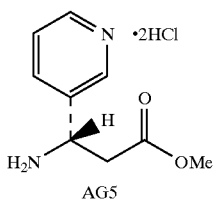

AG5

Particularly preferred compounds of the present invention include those compounds shown in Table 1 (and Table 2), where the letter "R" after the numeral "3" indicates the absolute configuration (Cahn-Ingold-Prelog rules).

TABLE II

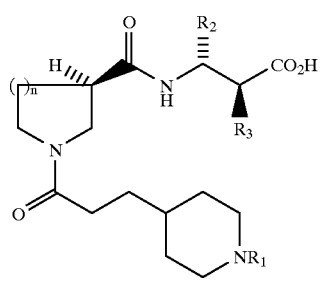

| # | n | R1 | R2 | R3 |
|---|---|----|----|----|
| 22 | 2 | H | H | NHCONH(3-MeOPh) |
| 23 | 2 | H | H | NHCOOCH$_2$Ph |
| 24 | 2 | H | H | NHCOOCH$_2$(3-ClPh) |
| 25 | 2 | H | H | NHSO2CH$_2$Ph |
| 26 | 2 | H | H | NHCONH(3,5-diMeOPh) |
| 27 | See structure below | | | |
| 28 | 2 | H | H | NHCONH(2-naphthyl) |
| 29 | See structure below | | | |
| 30 | 2 | H | H | NHCONHCH$_2$CH$_2$Ph |
| 31 | 2 | H | 6-Me-3-pyridyl | H |
| 32 | 2 | H | 5-Br-3-pyridyl | H |
| 33 | 2 | CH(NH) | 3-pyridyl | H |

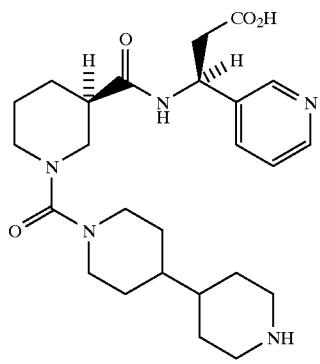

27

TABLE II-continued

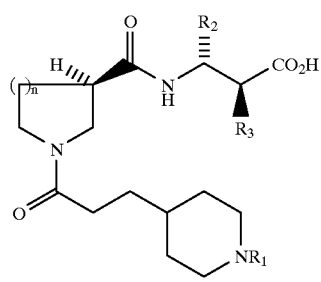

| # | n | R1 | R2 | R3 |
|---|---|----|----|----|

29

The diaminopropionic acid antagonists of the invention wherein $R_5$ is $C(O)NHQ(CHW)_rCO_2R_8$, $R_{10}$ is H, M is piperidin-1-yl and A is

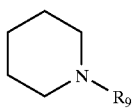

may be prepared as shown in Scheme AH. Methyl N-α-Z-diaminopropionate was acylated by HBTU-activated AH1, the Z group removed by hydrogenolysis to afford AH2 (for 23 the Z group was retained), and then the resultant primary amine reacted with the requisite isocyanate (or alkyl chloroformate for 24, alkylsulfonyl chloride for 25) to give AH3. The Boc group of intermediate AH3 was removed with HCl and the resultant secondary amine acylated with HBTU-activated AH4 to give AH5. This material was saponified with lithium hydroxide and the Boc group removed with HCl to give 22.

SCHEME AH

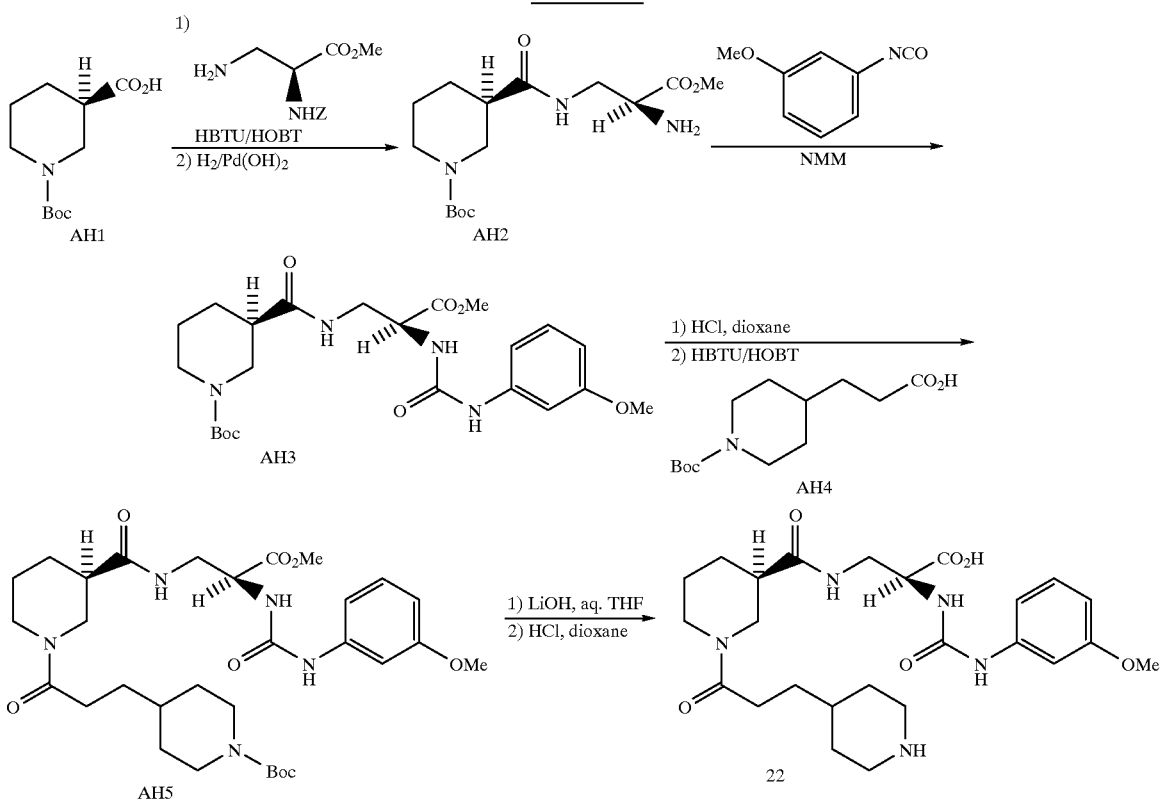

The bipiperidine-urea based antagonists of the invention may be prepared as shown in Scheme AJ. Intermediate AJ1 was prepared as described in Scheme AG. AJ1 was acylated with p-nitrophenyl chloroformate and then reacted with Boc-bipiperidine (for a synthesis, see W. Bondinell, patent application WO 94/14776). The ester AJ2 was saponified with lithium hydroxide and the Boc group removed with HCl to afford 27. Substituted piperidine aldehyde intermediates such as AK2 were prepared by lithium aluminum hydride reduction of their corresponding nicotinic acid methyl esters (AK1) followed by oxidation with manganese dioxide (Scheme AK). The aldehydes were then converted to β-amino acids as shown in Scheme AG. Formamidine AL3 was prepared as shown in Scheme AL. Amine AL1 was acylated with ethyl formimidate as described by M. K. Scott (*J. Med. Chem.* 1983, 26, 534). The ester AL2 was saponified with 4N HCl (RT, 20 h) to afford 33. Three-substituted β-amino acid-type antagonists were synthesized as shown in Scheme AM. Resolved 6-methyl-pyridyl-β-amino ester was acylated with HBTU-activated AM1, and the coupled product treated with HCl to afford amine AM2. The amine was acylated with HBTU-activated AM4, the ester saponified, and the Boc group removed with HCl to afford 31.

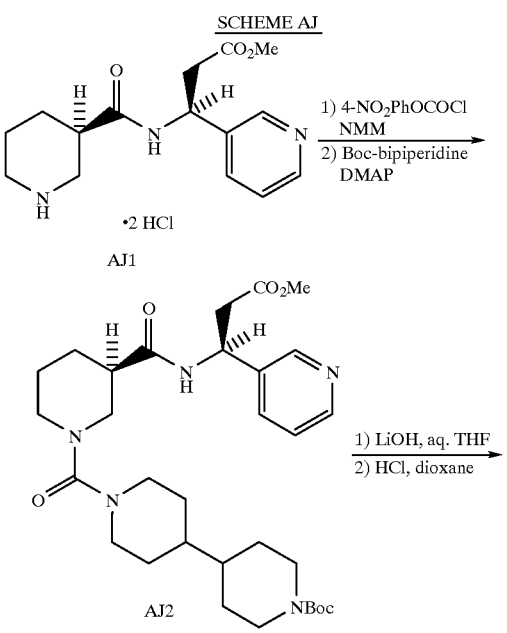

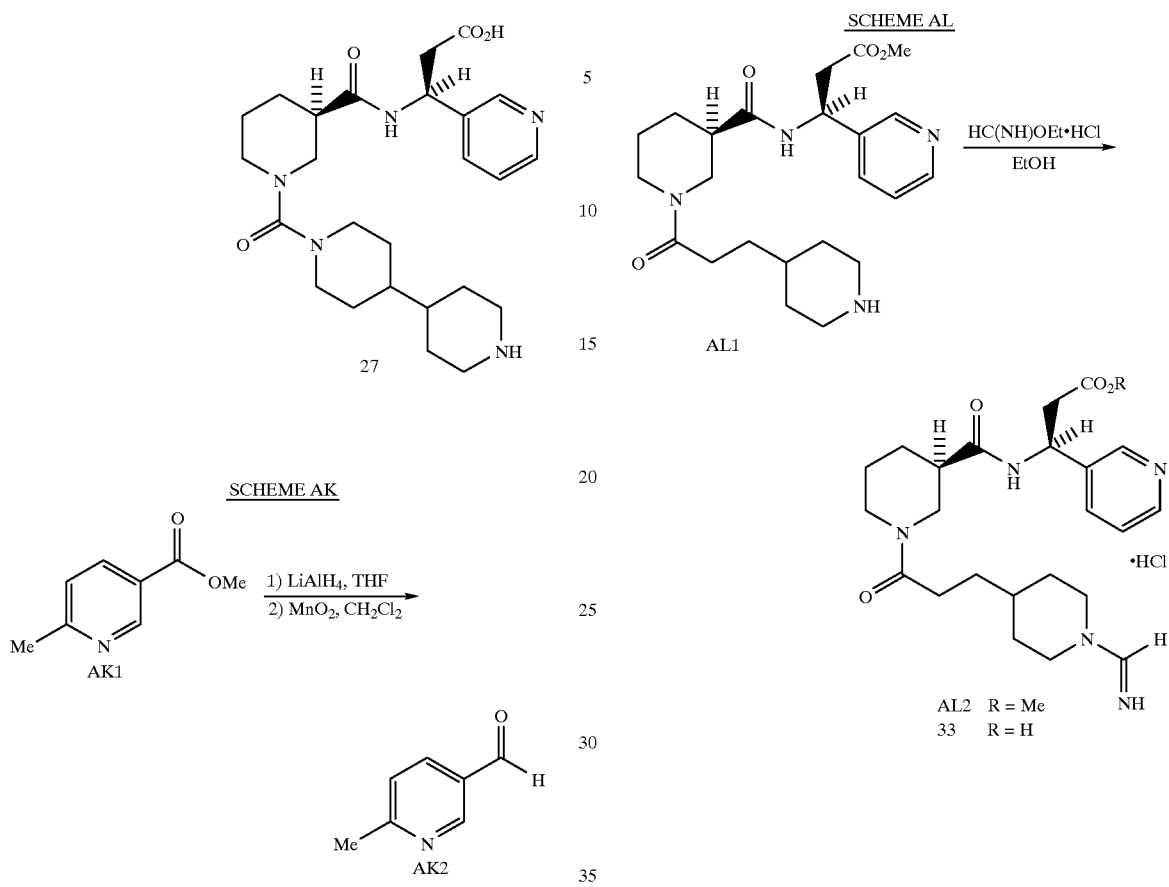
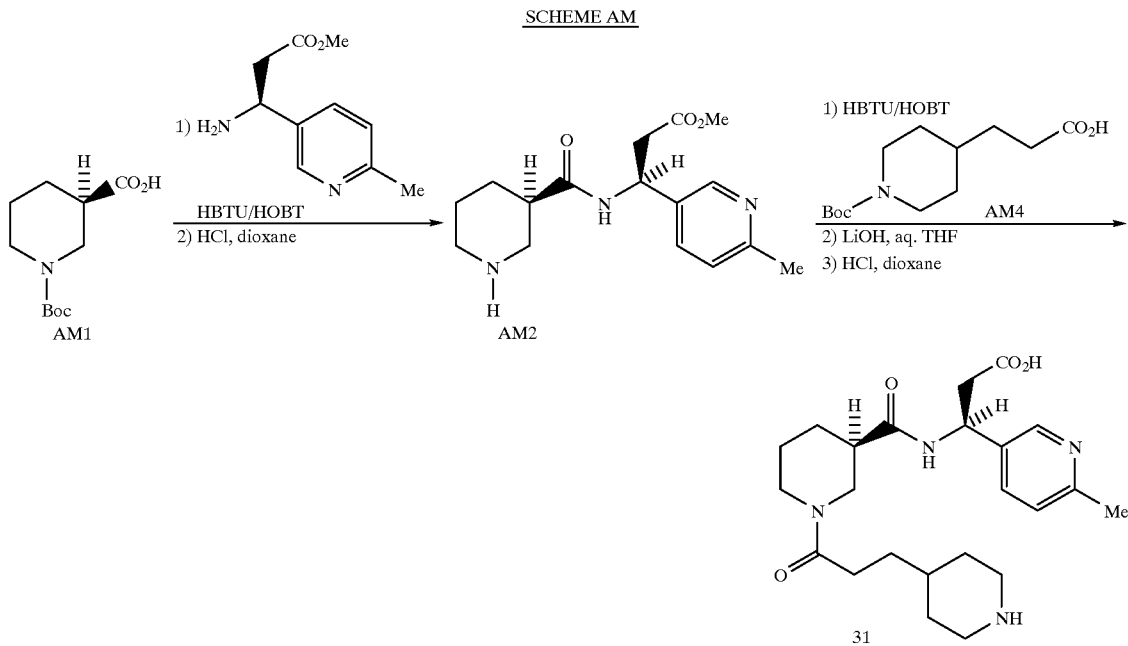

To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.03 mg to 100 mg/kg (preferred 0.1–30 mg/kg) and may be given at a dosage of from about 0.1–300 mg/kg/day (preferred 1–50 mg/kg/day). The dosages, however, may be varied depending upon the requirement of the patients, the severity of the condition being treated and the compound being employed. The use of either daily administration or post-periodic dosing may be employed.

BIOLOGY

The compounds of the present invention interrupt binding of fibrinogen to platelet glycoprotein IIb/IIIa (GPIIb/IIIa) and thereby inhibit platelet aggregation. Such compounds are, therefore, useful in treating platelet-mediated thrombotic disorders such as arterial and venous thrombosis, acute myocardial infarction, reocclusion following thrombolytic therapy and angioplasty, and a variety of vaso-occlusive disorders. Because the final, common pathway in normal platelet aggregation is the binding of fibrinogen to activated, exposed GPIIb/IIIa, inhibition of this binding represents a plausible antithrombotic approach. The receptor is activated by stimuli such as ADP, collagen, and thrombin, exposing binding domains to two different peptide regions of fibrinogen: α-chain Arg-Gly-Asp (RGD) and γ-chain 400–411. As demonstrated by the results of the pharmacological studies described hereinafter, the compounds of the present invention show the ability to block fibrinogen binding to isolated GPIIb/IIa ($IC_{50}$'s 0.0002–1.39 $\mu$M), inhibit platelet aggregation in vitro in the presence of a various of platelet stimuli (0.019–65.0 $\mu$M vs. thrombin), and furthermore, inhibit ex vivo platelet aggregation in animal models.

In Vitro Solid Phase Purified Glycoprotein IIB/IIIA Binding Assay

A 96 well Immulon-2 microtiter plate (Dynatech-Immulon) is coated with 50 $\mu$l/well of RGD-affinity purified GPIIb/IIIa (effective range 0.5–10 $\mu$g/mL) in 10 mM HEPES, 150 mM NaCl, 1 mM mgCl$_2$ at pH 7.4. The plate is covered and incubated overnight at 4° C. The GPIIb/IIIa solution is discarded and 150 $\mu$l of 5% BSA is added and incubated at RT for 1–3 h. The plate is washed extensively with modified Tyrodes buffer. Biotinylated fibrinogen (25 $\mu$l/well) at 2×final concentration is added to the wells that contain the test compounds (25 $\mu$l/well). The plate is covered and incubated at RT for 2–4 h. Twenty minutes prior to incubation completion, one drop of Reagent A (Vecta Stain ABC Horse Radish Peroxidase kit, Vector Laboratories, Inc.) and one drop Reagent B are added with mixing to 5 mL modified Tyrodes buffer mix and let stand. The ligand solution is discarded and the plate washed (5×200 $\mu$l/well) with modified Tyrodes buffer. Vecta Stain HRP-Biotin-Avidin reagent (50 $\mu$l/well, as prepared above) is added and incubated at RT for 15 min. The Vecta Stain solution is discarded and the wells washed (5×200 l/well) with modified Tyrodes buffer. Developing buffer (10 mL of 50 mM citrate/phosphate buffer @ pH 5.3, 6 mg Q-phenylenediamine, 6 $\mu$l 30% $H_2O_2$; 50 $\mu$l/well) is added and incubated at RT for 3–5 min, and then 2N $H_2SO_4$ (50 $\mu$l/well) is added. The absorbance is read at 490 nM. The results are shown in Tables III and IV.

In Vitro Inhibition of Thrombin-Induced Gel-Filtered Platelet Aggregation Assay

The percentage of platelet aggregation is calculated as an increase in light transmission of compound-treated platelet concentrate vs. control-treated platelet concentrate. Human blood is obtained from drug free, normal donors into tubes containing 0.13M sodium citrate. Platelet rich plasma (PRP) is collected by centrifugation of whole blood at 200×g for 10 min at 25° C. The PRP (5 mL) is gel filtered through Sepharose 2B (bed volume 50 mL), and the platelet count is adjusted to 2×10$^7$ platelets per sample. The following constituents are added to a siliconized cuvette: concentrated platelet filtrate and Tyrode's buffer (0.14M NaCl, 0.0027M KCl, 0.012M NaHCO$_3$, 0.76 mM Na$_2$HPO4, 0.0055M glucose, 2 mg/mL BSA and 5.0 mM HEPES @ pH 7.4) in an amount equal to 350 $\mu$l, 50 $\mu$l of 20 mM calcium and 50 $\mu$l of the test compound. Aggregation is monitored in a BIODATA aggregometer for the 3 min following the addition of agonist (thrombin 50 $\mu$l of 1 unit/mL). The results are shown in Tables III and IV.

TABLE III

| | In Vitro Results | | | |
|---|---|---|---|---|
| | Fibrinogen Binding | | Platelet Aggregation* | |
| Compound # | % Inh. (50 $\mu$M) | $IC_{50}$ ($\mu$M) | % Inh. (50 $\mu$M) | $IC_{50}$ ($\mu$M) |
| 1 | 95.0% | 0.003 | 83.0% | 3.6 |
| 2 | 93.0% | 0.027 | 95.7% | 54.0 |
| 3 | 81.0% | NT | 26.2% | >100 |
| 4 | 89.9% | 0.121 | 81.0% | 26.0 |
| 5 | 89.0% | 0.012 | 100% | 10.0 |
| 6 | 90.7 | 0.197 | 71.2% | 73.0 |
| 7 | 100% | 0.006 | 75.6% | 2.4 |
| 8 | 93.0% | 0.332 | 94.8% | 65.0 |
| 9 | 99.0% | 0.002 | 90.9% | 0.37 |
| 10 | 91.3% | 0.019 | 85.0% | 1.6 |
| 11 | 79.6% | 0.004 | 99.2% | 1.55 |
| 12 | 97.0% | 0.025 | 88.0% | 15.5 |
| 13 | 95.0% | 1.39 | 67.0% | 25.5 |
| 14 | 99.0% | 0.004 | 91.0% | 0.91 |
| 15 | 100% | 0.0091 | 92.2% | 1.9 |
| 16 | 100% | 0.0005 | 94.0% | 0.028 |
| 17 | 96.0% | 0.005 | 89.6% | 0.45 |
| 18 | 100% | 0.0002 | 100% | 0.019 |

TABLE III-continued

In Vitro Results

| | Fibrinogen Binding | | Platelet Aggregation* | |
|---|---|---|---|---|
| Compound # | % Inh. (50 μM) | IC$_{50}$ (μM) | % Inh. (50 μM) | IC$_{50}$ (μM) |
| 19 | 99.0% | 0.021 | 92.1% | 0.079 |
| 20 | 99.0% | 0.0007 | 89.7% | 37.0 |
| 21 | 100% | 0.0005 | 100% | 0.060 |

*Thrombin-induced aggregation of gel-filtered platelets.

TABLE IV

In Vitro Results

| | Fibrinogen Binding | | Platelet Aggregation* | |
|---|---|---|---|---|
| Compound # | % Inh. (50 μM) | IC$_{50}$ (μM) | % Inh. (50 μM) | IC$_{50}$ (μM) |
| 22 | 100% | 0.0007 | 94.0% | 0.046 |
| 23 | 100% | 0.0003 | 97.0% | 0.027 |
| 24 | 100% | 0.0004 | 100% | 0.018 |
| 25 | 100% | 0.0003 | 97.0% | 0.007 |
| 26 | 100% | 0.0003 | 97.0% | 0.016 |
| 27 | 100% | 0.0006 | 100% | 0.45 |
| 28 | 100% | 0.0002 | 100% | 0.17 |
| 29 | 100% | 0.068 | 100% | 42 |
| 30 | 100% | 0.0008 | 100% | 0.19 |
| 31 | 100% | 0.0003 | 100% | 0.045 |
| 32 | 100% | 0.0004 | 100% | 0.020 |
| 33 | 100% | 0.0007 | 100% | 0.30 |

*Thrombin-induced aggregation of gel-filtered platelets.

Ex Vivo Dog Study

Adult mongrel dogs (8–13 kg) were anesthetized with sodium pentobarbital (3 mg/kg, i.v.) and artificially respired. Arterial blood pressure and heart rate were measured using a Millar catheter-tip pressure transducer inserted in a femoral artery Another Millar transducer was placed in the left ventricle (LV) via a carotid artery to measure LV end diastolic pressure and indices of myocardial contractility. A lead electrocardiogram was recorded from limb electrodes. Catheters were placed in a femoral artery and vein to sample blood and infuse drugs, respectively. Responses were continuously monitored using a Modular Instruments data aquisition system.

Arterial blood samples (5–9 ml) were withdrawn into tubes containing 3.8% sodium citrate to prepare platelet rich plasma (PRP) and to determine effects on coagulation parameters: prothrombin time (PT) and activated partial thromboplastin time (APTT). Separate blood samples (1.5 ml) were withdrawn in EDTA to determine hematocrit and cell counts (platelets, RBC's and white cells). Template bleeding times were obtained from the buccal surface using a symplate incision devise and Whatman filter paper.

Aggregation of PRP was performed using a BioData aggregometer. Aggregation of whole blood used a Chronolog impedance aggregometer. PT and APTT were determined on either a BioData or ACL 3000+ coagulation analyser. Cells were counted with a Sysmex K-1000.

Compounds were solubilized in a small volume of dimethylformamide (DMF) and diluted with saline to a final concentration of 10% DMF. Compounds were administered by the intravenous route with a Harvard infusion pump. Doses was administered over a 15 min interval at a constant rate of 0.33 ml/min. Data were obtained after each dose and in 30 min intervals following the end of drug administration. Oral doses were administered as aqueous solutions via syringe.

Compounds caused marked inhibition of ex vivo platelet aggregation responses. Thus, in whole blood, the compounds inhibited collagen-stimulated (or ADP) aggregation in doses of 0.1–10 mg/kg with marked inhibition of collagen stimulated platelet ATP release. In PRP, the compounds also inhibited collagen stimulated platelet aggregaton with marked activity at 0.1–10 mg/kg. Compounds had no measurable hemodynamic effect in doses up to 1 mg/kg, iv. The drugs produce an increase in template bleeding time at 0.1–1 mg/kg with rapid recovery post treatment. No effects on coagulation (PT or APTT) were observed during treatment and platelet, white and RBC counts were unchanged at any dose of the compounds.

The results indicate that the compounds are broadly effective inhibitors of platelet aggregation ex vivo (antagonizing both collagen and ADP pathways) following iv administration of doses ranging from 0.1–1 mg/kg or 1–10 mg/kg orally (Tables V and VI). The antiaggregatory effects are accompanied by increases in bleeding time at the higher doses. No other hemodynamic or hematologic effects are observed.

TABLE V

Ex Vivo Dog Study Results

| | Intravenous Dosing | | Oral Dosing | |
|---|---|---|---|---|
| Compound # | Dose | Duration* | Dose | Duration* |
| 15 | 1 mpk | 30 min | 10 mpk | 120 min |
| 16 | 0.1 mpk | 60 min | 1 mpk | 60 min |
| | 0.3 mpk | NT | 3 mpk | >180 min |
| 18 | 0.1 mpk | 30 min | 1 mpk | 150 min |
| 19 | 1 mpk | 30 min | 10 mpk | 90 min |
| 21 | 0.3 mpk | 150 min | 1 mpk | 180 min |

*Indicates duration of >50% inhibition of collagen- or ADP-induced ex vivo platelet aggregation.

TABLE VI

Ex Vivo Dog Study Results

| | Intravenous Dosing | | Oral Dosing | |
|---|---|---|---|---|
| Compound # | Dose | Duration* | Dose | Duration* |
| 22 | 0.3 mpk | 180 min | 3 mpk | 60 min |
| 23 | 0.1 mpk | 60 min | 1 mpk | 180 min |
| | 0.3 mpk | NT | 3 mpk | 150 min |
| 24 | 0.3 mpk | 90 min | 3 mpk | 120 min |
| 25 | 0.3 mpk | 30 min | 3 mpk | 60 min |
| 26 | 0.3 mpk | NT | 3 mpk | 60 min |
| 27 | 0.3 mpk | 60 min | 3 mpk | 120 min |
| 28 | 0.3 mpk | NT | 3 mpk | 120 min |
| 30 | 0.3 mpk | 105 min | 3 mpk | 180 min |
| 31 | 0.3 mpk | 120 min | 3 mpk | >180 min |
| 31 | 0.3 mpk | 60 min | 3 mpk | 180 min |

*Indicates duration of >50% inhibition of collagen-induced ex vivo platelet aggregation.

Compounds 16 and 18 have shown efficacy in a canine arteriovenous shunt model of thrombosis in a dose-dependent fashion (method in "Nipecotic Acid Derivatives As Antithrombotic Compounds," application Ser. No. 08/213,772, filed Mar. 16, 1994). For instance, compound 16 inhibits thrombus formation at 10, 30, and 100 μg/kg/min cumulative doses by iv infusion (75%, 37%, 12% of thrombus weight vs. vehicle control, respectively). Compound 18 inhibits thrombus formation at 3, 10, and 30 μg/kg/min cumulative doses by iv infusion (82%, 41%, 12% of thrombus weight vs. vehicle control, respectively).

EXAMPLES

Protected amino acids were purchased from Aldrich Chemical or Bachem Bioscience Inc. 2-Chlorotrityl resin and Wang resin were obtained from Novabiochem Corp. Enantiomerically-enriched cycloalkylidene-3-carboxylic acid ethyl esters were isolated by chiral resolution of racemic material as published (A. M. Akkerman, *Rec. Trav. Chim. Pays-Bas* 1951, 70, 899). All other chemicals were purchased from Aldrich Chemical Company, Inc. Final product acid addition salts can be converted to free bases by basic ion exchange chromatography. High field $^1$H NMR spectra were recorded on a Bruker AC-360 spectrometer at 360 MHz, and coupling constants are given in Herz. Melting points were determined on a Mel-Temp II melting point apparatus and are uncorrected. Microanalyses were performed at Robertson Microlit Laboratories, Inc., Madison, N.J. In those cases where the product is obtained as a salt, the free base is obtained by methods known to those skilled in the art, e.g. by basic ion exchange purification. In the Examples and throughout this application, the following abbreviations have the meanings recited hereinafter.

Bn or Bzl=Benzyl
Boc=t-Butoxycarbonyl
BOC-ON=2-(t-Butoxycarbonyloxyimino)-2-phenylacetonitrile
BOP-Cl=Bis(2-oxo-3-oxazolidinyl)phosphinic chloride
CP=compound
DCE=1,2-Dichloroethane
DCM=Dichloromethane
DIBAL-H=Diisobutylaluminum hydride
DIC=Diisopropylcarbodiimide
DIEA=Diisopropylethylamine
DMAP=4-Dimethylaminopyridine
DMF=N,N-Dimethylformamide
EDC=Ethyl dimethylaminopropylcarbodiimide
EDTA=Ethylenediaminetetraacetic acid
Et$_2$O=Diethyl ether
HBTU=2-(1H-Benzotriazole-1-yl)-1,1,3,3-tetramethyluronium hexafluorophosphate
HOBT=Hydroxybenzotriazole
i-Pr=Isopropyl
KOTMS=Potassium trimethylsilanolate
NMM=N-Methylmorpholine
Nip=Nipecotyl (unless noted otherwise, racemic at 3-position)
NT=not tested
PPT=precipitate
PTSA=p-Toluenesulfonic acid
RT=room temperature
TFA=Trifluoroacetic acid
TMSN$_3$=Azidotrimethylsilane
Z=Benzyloxycarbonyl Allyl 3-(4-piperidine)propionate.HCl (AA1 precursor)

To a mixture of 3-(4-pyridine)acrylic acid (10.0 g, 0.066 mol) and aqueous HCl (2.0 N. 50 mL) under a blanket of nitrogen was added platinum (IV) oxide (0.54 g). This mixture was hydrogenated at 50 psi and RT for 21 h, filtered through Celite, and evaporated to give 3-(4-piperidine) propionic acid.HCl as a white powder (12.9 g, 99%). This powder was treated with allyl alcohol (50 mL) and warmed at 50° C. for 2 h. This solution was cooled to RT, evaporated to ca. 10 mL volume, and diluted with Et$_2$O (250 mL). The resultant precipitate was collected and washed with Et$_2$O to afford a white powder (14.5 g, 94%): $^1$H NMR (DMSO-d$_6$) δ 8.7–9.1 (m, 2H), 5.9 (m, 1H), 5.25 (dd, J=7, 15, 2H), 4.53 (d, J=4, 2H), 3.21 (d, J=8, 2H), 2.74 (t, J=7, 2H), 2.35 (t, J=4, 2H), 1.72 (d, J=8, 2H), 1.5 (m, 3H), 1.3 (m, 2H); MS m/e 198 (MH$^{+)}$.

Methyl (S)-3-amino-3-(3-pyridyl)propionate.2HCl (AG5)

Phenylacetamide intermediate AG3 was prepared using standard methods as shown in Scheme AG (E. Profft, *J. Prakt. Chem.* 1965, 30, 18). A mixture of AG1 (0.47 mol), EtOH (100 mL), NH$_4$OAc (0.47 mol), and malonic acid (0.70 mol) was heated at reflux for 6 h, cooled, and filtered. The white solid was washed with EtOH and MeOH and dried. This solid was dissolved in 2:1 acetone/water (360 mL), treated with triethylamine (0.72 mol) and phenylacetyl chloride (0.36 mol), and stirred for 22 h. The mixture was evaporated and the residue dissolved in water (500 mL) and adjusted to pH 12 (1 N NaOH). The aqueous layer was adjusted to pH 2 (conc. HCl), extracted with Et$_2$O, and evaporated to a white foam. The foam was purified by silica gel chromatography (10% MeOH/DCM) to give AG3. A solution of compound AG3 (0.22 mol) in water (600 mL) at RT was adjusted to pH 7.5 using KOH (3.0 N) and treated with penicillin amidase (91520 units, Sigma). This mixture was stirred for 47 h, acidified to pH 1 with HCl (conc), and the resultant ppt filtered through Celite. The filtrate was extracted with Et$_2$O (3×300 mL), concentrated in vacuo, and treated with MeOH/conc. NH$_4$OH (9:1). This product-containing solution was purified by silica gel chromatography (eluent DCM/MeOH/NH$_4$OH, 78:18:4) to give (S)-3-phenylacetamido-3-(3-pyridyl)propionic acid ammonium salt (19.5 g, 58%). This product was treated with HCl (6.0 N, 292 mL), heated at reflux for 5 h, cooled to RT, and extracted with Et$_2$O (3×200 mL). The aqueous layer was adjusted to pH 12, concentrated in vacuo, and the resultant solid triturated with MeOH (2×300 mL). This solution was evaporated to give ca. 14 g sodium salt. This material was treated with MeOH (500 mL), 2,2-dimethoxypropane (44 mL), and HCl (4 N in dioxane, 84 mL), and stirred for 90 h at RT. This mixture was filtered and the filtrate concentrated in vacuo. The resultant off-white solid was triturated with Et$_2$O (2×150 mL) and dried to give compound AG5 (16.7 g, 96% ee) as a white, amorphous solid.

Example 1
N-3-(4-Piperidinepropionyl)-nipecotyl-(3-amino-3-phenyl) propionic acid.TFA (1)

A 25 mL sintered glass vessel under nitrogen was charged with 2-chlorotrityl chloride resin (0.24 g, 0.36 mmol, Novabiochem) and DMF (5 mL). The resin was agitated with nitrogen for 5 min to swell and the DMF removed. The resin was treated with DMF (5 mL), DIEA (0.31 mL, 5 eq), and allyl 3-(4-piperidine)propionate.HCl (0.20 g, 2.4 eq), sequentially, and agitated for 8 h. The resultant dark green solution was removed, and the resin washed with DMF (3×5 mL), aqueous DMF (25%, 3×5 mL), THF (3×5 mL), DCM (3×5 mL), and Et$_2$O (5 mL). The resin was swelled with DCE (5 mL) and treated with a mixture of tetrabutylammonium fluoride hydrate (0.28 g, 3 eq), azidotrimethylsilane (0.38 mL, 10 eq), tetrakis(triphenylphosphine)palladium (0.084 g, 20 mol %), and DCE (5 mL). The resin was agitated for 15 h and the orange solution removed. The resin was washed with DCM (3×5 mL), DMF (3×5 mL), THF (3×5 mL), and Et$_2$O (5 mL). The resin was swelled with DMF (5 mL) and treated with DIEA (0.18 mL, 3 eq), allyl nipecotate.HCl (0.17 g, 3 eq), DIC (0.17 mL, 3 eq), and HOBT (1 mg). The resin was agitated for 15 h and then the reaction solution removed. The resin was washed with DMF (3×5 mL), aqueous DMF (25%, 3×5 mL), THF (3×5 mL), DCM (3×5 mL), and Et$_2$O (5 mL). The resin was swelled with DCE (5 mL) and treated with a mixture of tetrabutylammonium fluoride hydrate (0.28 g, 3 eq), azidotrimethylsilane (0.38 mL, 10 eq), tetrakis(triphenylphosphine) palladium (0.084 g, 20 mol %), and DCE (5 mL). The resin was agitated for 15 h and the orange solution removed. The resin was washed with DCM (3×5 mL), DMF (3×5 mL), THF (3×5 mL), and Et$_2$O (5 mL). The resin was swelled with DMF (5 mL) and treated with DIEA (0.18 mL, 3 eq), methyl D,L-3-amino-3-phenylpropionate.HCl (0.23 g, 3 eq), DIC (0.17 mL, 3 eq), and HOBT (1 mg). The resin was agitated for 17 h and then the reaction solution removed. The resin was washed with DMF (3×5 mL), aqueous DMF (25%, 3×5 mL), THF (3×5 mL), DCM (3×5 mL), and Et$_2$O (5 mL). The resin was swelled with THF (5 mL) and treated with a solution of KOTMS (0.23 g, 10 eq) and THF (2 mL). The resin was agitated for 18 h and then the reaction solution removed. The resin was washed with DMF (3×5 mL), acetic acid/THF (1:1, twice), aqueous DMF (25%, 3×5 mL), THF (3×5 mL), DCM (3×5 mL), and Et$_2$O (5 mL). The resin was treated with TFA/DCM (1:1, 10 mL), agitated for 15 min, and the resultant red solution collected. This solution was evaporated and the resultant oil triturated with Et$_2$O (3×5 mL) and dried to afford compound 1 as a clear glass (0.11 g): $^1$H NMR (DMSO-d$_6$) δ 8.6 (m, 1H), 8.42 (d, J=7, 1H), 8.2 (m, 1H), 7.3 (m, 3H), 7.2 (m, 2H), 5.18 (d, J=6, 1H), 4.3 (m, 1H), 3.7 (m, 1H), 3.2 (m, 3H), 2.8 (m, 2H), 2.6 (m, 2H), 2.3 (m, 5H), 1.1–1.9 (m, 11H); MS m/e 416 (MH$^+$).

Using the same general solid phase synthesis technique as described in Example 1, the compounds of indicated examples were made according to Scheme AA as recited in the particular example.

Example 2

N-(4-Piperidinemethylaminocarbonyl)-nipecotyl-(3-amino-2-methyl)propionic acid.TFA (2)

Compound 2 was prepared as shown in Scheme AA. Resin-bound 4-piperidinemethylamine (0.36 mmol) was swelled with DCE (5 mL), treated with p-nitrophenylchloroformate (0.36 mmol) and DIEA (0.36 mmol), agitated for 1 h, and the solvent removed. The resin was washed (see Example 1), swelled with DCE (5 mL), treated with allyl nipecotate.HCl (0.36 mmol) and DIEA (0.72 mmoL), and agitated for 16 h. The solvent was removed, the resin washed (see Example 1), and the allyl ester cleaved to the corresponding acid (see Example 1). The resin was swelled with DMF (5 mL), the acid coupled with methyl 3-amino-2-methylpropionate (0.36 mmol), and the synthesis completed as shown in Example 1. Compound 2 was isolated as a clear glass (0.11 g): $^1$H NMR (CD$_3$OD) δ 3.9 (m, 2H), 3.2 (m, 4H), 3.10 (d, J=7,2H), 2.9 (m, 3H), 2.6 (m, 2H), 2.3 (m, 1H), 1.9 (m, 4H), 1.7–1.9 (m, 5H), 1.3–1.5 (m, 5H), 1.11 (d, J=7, 3H); MS m/e 355 (MH$^+$).

Example 3

N-(4-Piperidinemethyloxycarbonyl)-nipecotyl-D-aspartic acid α-methyl ester.TFA (3)

Compound 3 was prepared as shown in Scheme AA. Resin-bound 4-piperidinemethanol (0.36 mmol) was swelled with DCE (5 mL), treated with p-nitrophenylchloroformate (0.36 mmol) and DIEA (0.36 mmol), agitated for 1 h, and the solvent removed. The resin was washed (see Example 1), swelled with DCE (5 mL), treated with allyl nipecotate.HCl (0.36 mmol) and DIEA (0.72 mmoL), and agitated for 16 h. The solvent was removed, the resin washed (see Example 1), and the allyl ester cleaved to the corresponding acid (see Example 1). The resin was swelled with DMF (5 mL), the acid coupled with H-D-Asp(OBn)-OMe (0.36 mmol), and the synthesis completed as shown in Example 1. Compound 3 was isolated as a yellow glass (0.019 g): $^1$H NMR (CD$_3$OD) δ 4.8 (m, 2H), 3.9 (m, 3H), 3.70 (d, J=9, 4H), 3.39 (s, 3H), 3.3 (m, 2H), 2.9 (m, 4H), 2.8 (m, 2H), 1.9 (m, 4H), 1.7 (m, 2H), 1.4 (m, 4H); MS m/e 400 (MH$^+$).

Example 4

N-3-(4-Piperidinepropionyl)-pyrrolidine-3-carboxy-[3-amino-3-(4-tolyl)]propionic acid.TFA (4)

Compound 3 was prepared as shown in Scheme AA. Intermediate AA2 (0.36 mmol) was swelled with DCE (5 mL), treated with methyl pyrrolidine-3-carboxylate.HCl (0.36 mmol), DIC (0.72 mmol), and DIEA (0.72 mmoL), and agitated for 16 h. The solvent was removed, the resin washed (see Example 1), and the methyl ester cleaved to the corresponding acid with KOTMS (see Example 1). The resin was swelled with DMF (5 mL), the acid coupled with methyl 3-amino-3-(4-tolyl)propionate (0.36 mmol), and then the synthesis completed as shown in Example 1. Compound 4 was isolated as a clear glass (0.081 g): $^1$H NMR (CD$_3$OD) δ 7.19 (d, J=5, 2H), 7.10 (d, J=5, 2H), 5.31 (dd, J=3, 10; 1H) 3.6 (m, 4H), 3.3 (m, 2H), 2.9 (m, 4H), 2.7 (m, 2H), 2.3(m, 2H), 2.1 (m, 3H), 1.9(m, 4H), 1.6 (m, 4H), 1.3 (m, 4H); MS m/e 416 (MH$^+$).

Example 5

N-3-(4-Piperidinepropionyl)-isonipecotyl-(3-amino-3-methyl) propionic acid.TFA (5)

Compound 5 was prepared as shown in Scheme AA. Intermediate AA2 (0.36 mmol) was swelled with DCE (5 mL), treated with ethyl isonipecotate (0.36 mmol), DIC (0.72 mmol), and DIEA (0.72 mmoL), and agitated for 16 h. The solvent was removed, the resin washed (see Example 1), and the ethyl ester cleaved to the corresponding acid with KOTMS (see Example 1). The resin was swelled with DMF (5 mL), the acid coupled with methyl 3-amino-3-methylpropionate (0.36 mmol), and then the synthesis completed as shown in Example 1. Compound 5 was isolated as a tan glass (0.033 g): $^1$H NMR (CD$_3$OD) δ 4.5 (m, 1H), 4.2 (m, 1H), 3.9 (m, 1H), 3.3 (m, 2H), 3.3 (m, 3H), 3.1 (m, 1H), 2.9 (m, 3H), 2.7 (m, 2H), 2.4 (m, 2H), 2.0 (m, 2H), 1.7 (m, 2H), 1.5 (m, 6H), 1.3 (m, 2H), 1.15 (d, J=9, 3H); MS m/e 354 (MH$^+$).

Example 6

N-3-(4-Piperidinepropionyl)-isonipecotyl-[3-amino-3-(4-carboxyphenyl)]propionic acid.TFA (6)

Compound 6 was prepared as shown in Scheme AA. Intermediate AA2 (0.36 mmol) was swelled with DCE (5 mL), treated with ethyl isonipecotate (0.36 mmol), DIC (0.72 mmol), and DIEA (0.72 mmoL), and agitated for 16 h. The solvent was removed, the resin washed (see Example 1), and the ethyl ester cleaved to the corresponding acid with KOTMS (see Example 1). The resin was swelled with DMF (5 mL), the acid coupled with methyl 3-amino-3-(4-carboxymethyl-phenyl)propionate (0.36 mmol), and then the synthesis completed as shown in Example 1. Compound 6 was isolated as a tan glass (0.034 g): $^1$H NMR (CD$_3$OD) δ 7.9 (m, 3H), 7.43 (d, J=5, 2H), 5.4 (m, 1H), 4.5 (m, 1H), 4.0 (m, 1H), 3.3 (m, 4H), 3.1 (m, 1H), 2.9 (m, 2H), 2.7 (m, 2H), 2.7 (m, 1H), 2.5 (m, 4H), 2.0 (m, 2H), 1.2–1.9 (m, 10H); MS m/e 460 (MH$^+$).

Example 7

N-3-(4-N-Methyl-piperidinepropionyl)-nipecotyl-3-aminopropionic acid.TFA (7)

Compound 7 was prepared as shown in Scheme AD. Resin-bound Fmoc-β-Ala (1 mmol) was treated with 20% piperidine/DMF (10 mL), agitated for 2 h, and the solvent removed. The resin was washed with DMF, swelled with DMF (10 mL), and treated with Fmoc-nipecotic acid (1 mmol), DIC (2 mmol), and DIEA (1 mmol). The resin was agitated for 16 h, the solvent removed, and the resin washed with DMF and DCM. The resin was treated with 20% piperidine/DMF (10 mL) for 2 h, the solvent removed, and the resin washed with DMF. The resin was swelled with DMF (10 mL), treated with 4-N-methylpiperidinepropionic acid (1 mmol), DIC (2 mmol), and DIEA (1 mmol), and agitated for 16 h. The solvent was removed and the resin washed with DMF and DCM. The resin was cleaved with 95% TFA (10 mL) and the TFA evaporated to afford 7 as a white powder (0.26 g): mp 172–177° C.; $^1$H NMR (CDCl$_3$) δ 4.4 (m, 1H), 3.7 (m, 1H), 3.4 (m, 1H), 3.2 (m, 1H), 3.1 (m, 1H), 2.7 (m, 2H), 2.3 (m, 6H), 2.21 (s, 3H), 1.9 (m, 4H), 1.3–1.8 (m, 10H); MS m/e 354 (MH$^+$).

Example 8

N-3-(4-Piperidinepropionyl)-nipecotyl-4-oxonipecotic acid.TFA (8)

Compound 8 was prepared as shown in Scheme AA. Intermediate AA2 (0.36 mmol) was swelled with DCE (5 mL), treated with ethyl nipecotate (0.36 mmol), DIC (0.72 mmol), and DIEA (0.72 mmoL), and agitated for 16 h. The solvent was removed, the resin washed (see Example 1), and the ethyl ester cleaved to the corresponding acid with KOTMS (see Example 1). The resin was swelled with DMF (5 mL), the acid coupled with methyl 4-oxo-nipecotate (0.36 mmol), and then the synthesis completed as shown in Example 1. Compound 8 was isolated as a dear glass (0.04 g): $^1$H NMR (DMSO-d$_6$) δ 8.5 (m, 1H), 8.2 (m, 1H), 6.5 (m, 1H), 4.3 (m, 1H), 3.4–3.8 (m, 4H), 3.2 (m, 2H), 3.0 (m, 1H), 2.8 (m, 2H), 2.2–2.6 (m, 6H), 1.8 (m, 2H), 1.1–1.7 (m, 11H); MS m/e 394 (MH$^+$).

Example 9

N-3-(4-Piperidinepropionyl)-nipecotyl-[3-amino-3-(2-trimethylsilylethynyl)]propionic acid.TFA (9)

Compound 9 was prepared as shown in Scheme AA. Intermediate AA2 (0.36 mmol) was swelled with DCE (5 mL), treated with ethyl nipecotate (0.36 mmol), DIC (0.72 mmol), and DIEA (0.72 mmoL), and agitated for 16 h. The solvent was removed, the resin washed (see Example 1), and the ethyl ester cleaved to the corresponding acid with KOTMS (see Example 1). The resin was swelled with DMF (5 mL), the acid coupled with methyl 3-amino-3-(2-trimethylsilylethynyl)propionate (for a preparation, see J. Zablocki, *J. Med. Chem.* 1995, 38, 2378; 0.36 mmol), and then the synthesis completed as shown in Example 1. Compound 9 was isolated as a yellow glass (0.12 g): $^1$H NMR (CD$_3$OD) δ 3.8 (m, 1H), 3.2–3.4 (m, 4H), 2.9 (m, 3H), 2.7 (m, 2H), 2.3–2.5 (m, 2H), 1.9 (m, 4H), 1.1–1.9 (m, 13H), 0.0 (s, 9H); MS m/e 436 (MH$^+$).

Example 10

N-(6-Aminocaproyl)-nipecotyl-3-amino-3-(3-pyridyl) propionic acid.3TFA (10)

Compound 10 was prepared as shown in Scheme AA. Resin-bound 6-aminocaproic acid (0.36 mmol) was swelled with DCE (5 mL), treated with ethyl nipecotate (0.36 mmol), DIC (0.72 mmol), and DIEA (0.72 mmoL), and agitated for 16 h. The solvent was removed, the resin washed (see Example 1), and the ethyl ester cleaved to the corresponding acid with KOTMS (see Example 1). The resin was swelled with DMF (5 mL), the acid coupled with methyl 3-amino-3-(3-pyridyl)propionate (0.36 mmol), and then the synthesis completed as shown in Example 1. Compound 10 was isolated as a clear glass (0.008 g): $^1$H NMR (DMSO-d$_6$) δ 8.6 (m, 2H), 8.1 (s, 1H), 7.0–7.7 (m, 5H), 5.15 (t, J=3, 1H), 4.4 (m, 1H), 4.1 (m, 1H), 3.7 (m, 2H), 3.1 (m, 1H), 2.7 (m, 4H), 2.5 (m, 1H), 2.3 (m, 2H), 1.2–1.9 (m, 11H); MS m/e 391 (MH$^+$). Anal. calcd. for C$_{20}$H$_{30}$N$_4$O$_4$.3TFA.2H$_2$O (768.60): C, 40.63; H, 4.85; N, 7.29; F, 22.25. Found: C, 40.81; H, 4.70; N, 6.12; F, 23.83.

Example 11

N-3-(4-Piperidinepropionyl)-R-(−)-nipecotyl-(3-amino-2-hydroxy) propionic acid.TFA (11)

Compound 11 was prepared as shown in Scheme AA. Intermediate AA2 (0.36 mmol) was swelled with DCE (5 mL), treated with ethyl R-nipecotate (0.36 mmol), DIC (0.72 mmol), and DIEA (0.72 mmoL), and agitated for 16 h. The solvent was removed, the resin washed (see Example 1), and the ethyl ester cleaved to the corresponding acid with KOTMS (see Example 1). The resin was swelled with DMF (5 mL), the acid coupled with methyl 3-amino-2-hydroxypropionate (0.36 mmol), and then the synthesis completed as shown in Example 1. Compound 11 was isolated as a pink glass (0.05 g): $^1$H NMR (DMSO-d$_6$) δ 8.5 (m, 1H), 8.2 (m, 1H), 7.6 (m, 1H), 4.0–4.4 (m, 2H), 3.7 (m, 1H), 3.2 (m, 3H), 2.8 (m, 3H), 2.6 (m, 1H), 2.1–2.3 (m, 3H), 1.8 (m, 4H), 1.0–1.4 (m, 10H); MS m/e 356 (MH$^+$).

Example 12

N-3-(4-Piperidineethanesulfonyl)-nipecotyl-3-aminopropionic acid.HCl (12)

Compound 12 was prepared as shown in Scheme AE. Intermediate AE1 was synthesized by the following procedure. 2-(4-Pyridine)ethanesulfonic acid (3.0 g, 0.016 mol) was dissolved in aq. HCl (2.0 N, 12 mL) and this solution treated with platinum dioxide (0.13 g) and hydrogenated at 50 psi and RT for 18 h. This mixture was filtered through Celite and evaporated to afford 2-(4-piperidine) ethanesulfonic acid.HCl (3.5 g, white powder). This powder was dissolved in aq. THF (1:1, 70 mL) at RT and treated with NMM (3.7 mL, 2.2 eq.) and benzyl chloroformate (2.2 mL, 1 eq.). This mixture was stirred for 15 h, acidified with aq. citric acid, and extracted with CHCl$_3$ (2×100 mL). The organic layer was dried with Na$_2$SO$_4$ and evaporated to afford 2-(4-N-Z-piperidine)ethanesulfonic acid (2.75 g, gold oil). This oil was converted to final product 12 in five synthetic steps (Scheme AE, W. J. Hoekstra, *J. Med. Chem.* 1995, 38,1582) and isolated as a clear glass (0.060 g): $^1$H NMR (DMSO-d$_6$) δ 8.9 (m, 1H), 8.6 (m, 1H), 3.5 (m, 2H), 3.1–3.3 (m, 4H), 3.0 (m, 2H), 2.6–2.8 (m, 4H), 2.3 (m, 3H), 1.65–1.9 (m, 5H), 1.6 (m, 3H), 1.2–1.4 (m, 5H); MS m/e 376 (MH$^+$).

Example 13

N-3-(4-Piperidinepropionyl)-nipecotyl-5H-(2-aminoethyl) tetrazole.HCl (13)

Compound 13 was prepared as shown in Scheme AC. Intermediate AC1 (prepared as in W. J. Hoekstra, *J. Med. Chem.* 1995, 38,1582; 1.9 mmol) was dissolved in DCM (50 mL) and treated with BOP-Cl (1.9 mmol), NMM (1.9 mmol), and 3-aminopropionitrile (1.9 mmol). The reaction was stirred for 18 h, diluted with sat'd NH$_4$Cl, and the layers separated. The organic layer was evaporated and the product purified by silica gel chromatography (10% EtOH/DCM) to give an oil. The oil was dissolved in toluene (10 mL), treated with azidotrimethylsilane (2.4 mmol) and dibutyltin oxide (1.2 mmol), and heated at reflux for 16 h. Cooling gave a brown ppt which was triturated with Et$_2$O. This solid was hydrogenated over platinum dioxide (0.08 g) in MeOH (12 mL) at 50 psi for 15 h, filtered, and evaporated to give 13 as a yellow foam (0.065 g): $^1$H NMR (DMSO-d$_6$) δ 8.9 (m, 1H), 8.6 (m, 1H), 8.13 (d, J=28, 1H), 4.2 (m, 2H), 3.2 (m, 3H), 3.0 (m, 4H), 2.7 (m, 4H), 2.31 (q, J=8, 2H), 1.7–1.9 (m, 3H), 1.4–1.6 (m, 5H), 1.1–1.3 (m, 4H); MS m/e 364 (MH$^+$).

Example 14
N-3-(4-N-Methyl-piperazinepropionyl)-nipecotyl-[3-amino-3-(3.4-methylenedioxyphenyl)]propionic acid.Na (14)

Compound 14 was prepared as shown in Scheme AB. Ethyl nipecotate (3 mmol) was dissolved in DCM (50 mL), treated with acryloyl chloride (3 mmol) and NMM (3 mmol), and stirred for 1 h. The solvent was evaporated and the residue dissolved in EtOH (50 mL) and treated with N-methylpiperazine (3 mmol). The solution was warmed at 60° C. for 15 h, cooled to RT, and the solvent evaporated. The residue was partitioned between DCM (100 mL) and water (10 mL), and the layers separated. The organic layer was dried and evaporated to give a foam. The foam was dissolved in water, treated with NaOH (3 mmol), stirred for 1 h, and evaporated to give AB3.Na. The synthesis was completed as illustrated (W. J. Hoekstra, *J. Med. Chem.* 1995, 38, 1582) using methyl 3-amino-3-(3,4-methylenedioxyphenyl)propionate (2.5 mmol) to give 14 as a white, amorphous solid (0.14 g): $^1$H NMR (D$_2$O) δ 6.8 (m, 3H), 5.91 (s, 2H), 5.0 (m, 1H), 4.0 (m, 1H), 3.7 (m, 1H), 2.8–3.4 (m, 11H), 2.69 (s, 3H), 2.4–2.6 (m, 7H), 1.9 (m, 1H), 1.7 (m, 2H), 1.5 (m, 1H); MS m/e 475 (MH$^+$). Anal. calcd. for C$_{24}$H$_{33}$N$_4$O$_6$.Na.H$_2$O (514.56): C, 56.02; H, 6.86; N, 10.89. Found: C, 55.72; H, 6.78; N, 10.52.

Example 15
N-3-(4-N-Methyl-piperazinepropionyl)-nipecotyl-[3-amino-3-(3-quinolinyl)]propionic acid.3TFA (15)

Compound 15 was prepared as described in Example 14. The synthesis was completed as illustrated (W. J. Hoekstra, *J. Med. Chem.* 1995, 38, 1582) using methyl 3-amino-3-(3-quinolinyl)propionate (6 mmol) with AB3. Compound 15 was isolated as a yellow powder (1.89 g): $^1$H NMR (DMSO-d6) δ 8.94 (s, 1H), 8.12 (s, 1H), 7.9 (m, 2H), 7.6 (m, 2H), 7.07 (d, J=4, 1H), 5.2 (m, 1H), 4.1 (m, 1H), 3.7 (m, 1H), 3.1–3.3 (m, 2H), 2.9 (m, 2H), 2.6 (m, 2H), 2.43 (s, 3H), 1.9–2.4 (m, 12H), 1.2–1.5 (m, 4H); MS m/e 482 (MH$^+$).

Example 16
N-3-(4-Piperidinepropionyl)-R-(−)-nipecotyl-[(S)-3-amino-3-(3,4-methylenedioxyphenyl)]propionic acid.HCl (16)

To a cooled (5° C.) solution of Boc-R-nipecotic acid (9 mmol) and methyl (S)-3-amino-3-(3,4-methylenedioxyphenyl)]propionate (see AG5 example; 9 mmol) in MeCN (100 mL) was added HBTU (9 mmol), HOBT (9 mmol), and NMM (18 mmol). This mixture was stirred for 15 h, diluted with water (10 mL), and evaporated. The residue was diluted with EtOAc (100 mL) and the organic layer dried and evaporated to give a white foam. The foam was treated with HCl (2 N in dioxane, 20 mL), stirred for 3 h, and evaporated to a foam. The foam was dissolved in MeCN (100 mL) and treated with Boc-piperidinepropionic acid (7 mmol), HBTU (7 mmol), HOBT (7 mmol), and NMM (14 mmol) with stirring for 6 h. The mixture was diluted with water (10 mL), evaporated, and diluted with EtOAc (100 mL). The organic layer was dried, evaporated, and purified by silica gel chromatography (7% EtOH/DCM) to give a foam. To a solution of the foam (4.6 mol) in THF cooled in an ice bath was added LiOH.H$_2$O (6.9 mmol dissolved in 30 mL water) dropwise. This mixture was stirred for 1.5 h, acidified with AcOH (1.7 mL), and warmed to RT. This solution was diluted with CHCl$_3$ (75 mL) and the layers separated. The organic layer was dried (Na$_2$SO$_4$) and evaporated to give a white foam. The foam was dissolved in dioxane (20 mL) and anisole (0.3 mL), cooled in an ice bath, treated with HCl (15 mL, 4.0 N in dioxane), and stirred for 3 h to give a ppt. The ppt was filtered and washed with Et$_2$O (150 mL) and MeCN (20 mL) to give 16 as a white powder (1.78 g): mp 190–200° C.; $^1$H NMR (DMSO-d$_6$) δ 8.9 (m, 1H), 8.6 (m, 1H), 8.4 (m, 1H), 6.83 (d, J=5, 1H), 6.79 (d, J=5, 1H), 6.7 (m, 1H), 5.95 (s, 2H), 5.08 (dd, J=5, 11, 1H), 4.1–4.3 (m, 1H), 3.7 (m, 1H), 3.15 (d, J=10, 2H), 3.0 (m, 1H), 2.7 (m, 2H), 2.6 (m, 3H), 2.31 (d, J=7, 2H), 1.81 (d, J=10, 2H), 1.2–1.7 (m, 11H); MS m/e 460 (MH$^+$); [α]$^{24}$D −0.478° (c 1.00, MeOH).

Example 17
N-3-(4-Piperidinepropionyl)-hexahydroazepine-3-carboxy-[3-amino-3-(3-quinolinyl)]propionic acid.2TFA (17)

Compound 17 was prepared as shown in Scheme AA. Intermediate AA2 (0.36 mmol) was swelled with DCE (5 mL), treated with methyl hexahydroazepine-3-carboxylate.HCl (0.36 mmol), DIC (0.72 mmol), and DIEA (0.72 mmoL), and agitated for 16 h. The solvent was removed, the resin washed (see Example 1), and the methyl ester cleaved to the corresponding acid with KOTMS (see Example 1). The resin was swelled with DMF (5 mL), the acid coupled with methyl 3-amino-3-(3-quinolinyl)propionate (0.36 mmol), and then the synthesis completed as shown in Example 1. Compound 17 was isolated as a glass (0.10 g): $^1$H NMR (D$_2$O) δ 9.06 (s, 1H), 8.9 (m, 1H), 8.2 (m, 1H), 8.04 (s, 1H), 8.0 (t, J=4, 2H), 7.8 (t, J=4, 2H), 5.5 (m, 1H), 3.8 (m, 1H), 3.3 (m, 4H), 3.0 (m, 2H), 2.7 (m, 4H), 2.0–2.4 (m, 6H), 1.7–1.9 (m, 4H), 1.1–1.6 (m, 8H); MS m/e 481 (MH$^+$).

Example 18
N-3-(4-Piperidinepropionyl)-R-(−)-nipecotyl-[(S)-3-amino-3-(3-quinolinyl)]propionic acid.2HCl (18)

Compound 18, prepared as described in Example 16 starting with Boc-R-nipecotic acid (7.1 mmol) and methyl (S)-3-amino-3-(3-quinolinyl)propionate (see example AG5; 7.1 mmol), was isolated as white flakes (1.11 g): mp 142–144° C.; MS m/e 467 (MH$^+$); [α]$^{24}$D -173° (c 0.1, MeOH). Anal. calcd. for C$_{26}$H$_{34}$N$_4$O$_4$.2.25 HCl.H$_2$O (566.64): C, 55.1 1; H, 6.80; N, 9.89; Cl, 14.08. Found: C, 54.85; H, 6.62; N, 10.04; Cl, 13.68.

Example 19
N-3-(4-Piperidinepropionyl)-R-(−)-nipecotyl-[(S)-3-amino-3-(2-t-butylethynyl)]propionic acid.HCl (19)

Compound 19, prepared as described in Example 16 starting with Boc-R-nipecotic acid (3.2 mmol) and methyl (S)-3-amino-3-(2-t-butylethynyl)propionate (see J. A. Zablocki, *J. Med. Chem.* 1995, 38, 2378; 3.2 mmol), was isolated as a white powder (0.33 g): MS m/e 420 (MH$^+$). Anal. calcd. for C23H$_{37}$N$_3$O$_4$.1.07 HCl.0.43H$_2$O (468.97): C, 59.21; H, 8.42; N, 8.96; Cl, 8.09. Found: C, 58.92; H, 8.58; N, 8.76; Cl, 7.82.

Example 20
N-3-(4-Piperidinepropyl)-nipecotyl-[(S)-3-amino-3-(3,4-methylenedioxyphenyl)]propionic acid.2TFA (20)

Compound 20 was prepared as shown in Scheme AF. Intermediate AF3 (2.8 mmol) was dissolved in benzene (50 mL), treated with ethyl nipecotate (2.8 mmol), and heated at reflux for 7 h. The reaction was cooled, partitioned between water (15 mL) and EtOAc (70 mL), and the layers separated. The organic layer was dried and evaporated to give AF4. AF4 was converted to 20 as previously described (W. J. Hoekstra, *J. Med. Chem.* 1995, 38, 1582) and isolated as a white powder (0.33 g): $^1$H NMR (CD$_3$OD) δ 8.6–8.8 (m, 3H), 6.7–6.9 (m, 3H), 5.91 (s, 2H), 5.1–5.2 (m, 1H), 3.3–3.5 (m, 4H), 2.8–3.1 (m, 6H), 2.6–2.7 (m, 3H), 1.5–2.0 (m, 11H), 1.2–1.4 (m, 4H); MS m/e 446 (MH$^+$).

Example 21
N-3-(4-Piperidinepropionyl)-R-(−)-nipecotyl-[(S)-3-amino-3-(3-pyridyl)]propionic acid.2TFA (21)

Compound 21, prepared as described in Example 16 starting with Boc-R-nipecotic acid (6.4 mmol) and methyl (S)-3-amino-3-(3-pyridyl)propionate (see example AG5; 6.4 mmol), was isolated as a white amorphous solid (1.60 g): mp 74–81° C.; MS m/e 417 (MH$^+$). Anal. calcd. for $C_{22}H_{32}N_4O_4$.2.1 $C_2HF_3O_2$.0.7$H_2O$ (668.58): C, 47.07; H, 5.35; N, 8.38; F, 17.90; KF, 1.89. Found: C, 47.08; H, 5.31; N, 8.41; F, 17.68; KF, 2.00.

Example 22
N-3-(4-Piperidinepropionyl)-R-(−)-nipecotyl-[(S)-2-(3-methoxyanilino)carbonylamino-3-amino]propionic acid (22)

Methyl Boc-R-nipecotyl-[(S)-2-Z-amino-3-amino]propionate (prepared from methyl N-α-Z-L-diaminopropionate and Boc-R-nipecotic acid as shown in Example 16; 9.5 mmol) was dissolved in MeOH (40 mL) and hydrogenated at 50 psi over palladium hydroxide (0.4 g) for 24 h. The mixture was filtered and evaporated to give white solid AH2. AH2 (9.1 mmol) was dissolved in DCM (100 mL), cooled (5° C.), treated with 3-methoxyphenylisocyanate (9.1 mmol) and NMM (9.1 mmol), and stirred for 17 h. The solution was diluted with sat'd NH$_4$Cl (10 mL), the layers separated, and the organic layer dried, evaporated to an oil, and purified by silica gel chromatography (4% EtOH/DCM) to give AH3. Intermediate AH3 was converted to 22 in four steps as in Example 16 to afford a white amorphous solid (1.35 g): mp 72–76° C.; $^1$H NMR (DMSO-d$_6$) δ 8.7 (m, 3H), 7.8 (m, 1H), 7.1 (m, 2H), 6.8 (d, 1H), 6.5 (d, 2H), 3.66 (s, 3H), 3.4 (m, 2H), 3.2 (d, 2H), 2.7 (dd, 4H), 2.3 (m, 3H), 1.6 (m, 3H), 1.1–1.7 (m, 11H); MS m/e 504 (MH$^+$). Anal. calcd. for $C_{25}H_{37}N_5O_6$.1.2 HCl.1.0$H_2O$ (565.37): C, 53.11; H, 7.17; N, 12.39; Cl, 7.53. Found: C, 53.40; H, 7.44; N, 12.14; Cl, 7.66.

Using the same general synthesis technique as described in Example 22, the compounds of Examples 26, 28–30 were made according to Scheme AH recited in the particular example. For carbamate analogues, the acylating agent employed was the appropriate alkyl chloroformate (analogous conversion of AH2 to AH3; one molar equivalent). For sulfonamides, the sulfonating agent employed was the appropriate sulfonyl chloride (one molar equivalent).

Example 23
N-3-(4-Piperidinepropionyl)-R-(−)-nipecotyl-[(S)-2-benzyloxycarbonylamino-3-amino]propionic acid.HCl (23)

Compound 23, prepared from methyl N-α-Z-L-diaminopropionate (8.8 mmol) and Boc-R-nipecotic acid (8.8 mmol) as shown in Example 16, was isolated as a white powder (1.65 g): mp 110–113° C.; MS m/e 489 (MH$^+$). Anal. calcd. for $C_{25}H_{36}N_4O_6$.1.15 HCl.0.5$H_2O$.0.5 Dioxane (583.57): C, 55.56; H, 7.41; N, 9.60; Cl, 6.99. Found: C, 55.23; H, 7.79; N, 9.85; Cl, 7.01.

Example 24
N-3-(4-Piperidinepropionyl)-R-(−)-nipecotyl-[(S)-2-(3-chlorobenzyloxy)carbonylamino-3-amino]propionic acid.HCl (24)

Compound 24, prepared by reacting 3chlorobenzyloxycarbonyl chloride (6.6 mmol) with AH2 (6.6 mmol) as described in Example 22, was isolated as a white amorphous solid (1.33 g): mp 89–96° C.; MS m/e 524 (MH$^+$). Anal. calcd. for $C_{25}H_{35}ClN_4O_6$.1.25 HCl.0.5$H_2O$.1.0 Dioxane (637.20): C, 50.89; H, 7.08; N, 8.78; Cl, 12.52. Found: C, 51.10; H, 6.71; N, 8.38; Cl, 12.20.

Example 25
N-3-(4-Piperidinepropionyl)-R-(−)-nipecotyl-[(S)-2-benzylsulfonylamino-3-amino]propionic acid.HCl (25)

Compound 25, prepared by reacting benzylsulfonyl chloride (5.2 mmol) with AH2 (5.2 mmol) as shown in Example 22, was isolated as a white powder (0.87 g): mp 145–149° C.; MS m/e 509 (MH$^+$). Anal. calcd. for $C_{24}H_{36}N_4O_6S$.1.3 HCl.0.3 Dioxane (568.06): C, 50.75; H, 7.04; N, 9.86; Cl, 8.11. Found: C, 51.03; H, 6.93; N, 9.46; Cl, 7.85.

Example 26
N-3-(4-Piperidinepropionyl)-R-(−)-nipecotyl-[(S)-2-(3,5-dimethoxyanilino)carbonylamino-3-amino]propionic acid.HCl (26)

Compound 26, prepared by reacting 3,5-dimethoxyphenylisocyanate (10.2 mmol) with AH2 (10.2 mmol) as shown in Example 22, was isolated as a white powder (1.89 g): mp 190–193° C.; MS m/e 534 (MH$^+$). Anal. calcd. for $C_{26}H_{39}N_5O_7$. 1.2 HCl.0.2 Dioxane (585.40): C, 53.35; H, 7.20; N, 11.96; Cl, 7.27. Found: C, 53.48; H, 7.38; N, 12.05; Cl, 6.97.

Example 27
N-[(4,4'-Bipiperidin-1-yl-)carbonyl]-R-(−)-nipecotyl-[(S)-3-amino-3-(3-pyridyl)]propionic acid.3HCl (27)

Intermediate AJ1 (5.5 mmol), prepared as shown in Example 16, was dissolved in DCM (140 mL), cooled (5° C.), treated with p-nitrophenylchloroformate (5.5 mmol) and (16.5 NMM mmol), and stirred for 2 h. The mixture was diluted with water (15 mL), the layers separated, and the organic layer dried and evaporated to an oil. The oil was dissolved in MeCN (70 mL), treated with N-Boc-4,4'-bipiperidine (7.5 mmol) and DMAP (5.5 mmol), and heated at reflux for 24 h. The mixture was cooled, evaporated to a solid, and partitioned between EtOAc (150 mL) and NaOH (1 N, 20 mL). The layers were separated, and the organic layer dried, evaporated to a solid, and purified by silica gel chromatography (8% EtOH/DCM) to give green glass AJ2 (1.5 mmol). AJ2 was saponified and deprotected as described in Example 16 to give 27 as a pale yellow powder (0.73 g): mp 121–125° C.; MS m/e 472 (MH$^+$). Anal. calcd. for $C_{25}H_{37}N_5O_4$.3.6 HCl.1.0 Dioxane (690.98): C, 50.41; H, 7.09; N, 10.14; Cl, 18.47. Found: C, 50.80; H, 7.31; N, 10.20; Cl, 18.78.

Example 28
N-3-(4-Piperidinepropionyl)-R-(−)-nipecotyl-[(S)-2-(2-naphthylamino)carbonylamino-3-amino]propionic acid.HCl (28)

Compound 28, prepared by reacting 2-naphthylisocyanate (8.5 mmol) with AH2 (8.5 mmol) as shown in Example 22, was isolated as a white powder (1.65 g): mp 187–193° C.; MS m/e 524 (MH$^+$). Anal. calcd. for $C_{28}H_{37}N_5O_5$.1.36 HCl.0.72 Dioxane (602.07): C, 55.86; H, 7.39; N, 11.63; Cl, 8.01. Found: C, 56.03; H, 7.11; N, 11.23; Cl, 7.97.

Example 29
N-3-(4-Piperidinepropionyl)-R-(−)-nipecotyl-aminomethyl-5-(S)-(3-N-benzyl)imidazoline-2,4-dione.HCl (29)

N-3-(4-Piperidinepropionyl)-R-(−)-nipecotyl-[(S)-2-(2-benzylamino)carbonylamino-3-amino]propionic acid hydrochloride (0.15 g), prepared from intermediate AH2 (4.4 mmol) and benzylisocyanate (4.4 mmol) as described in Example 22, was dissolved in aq. HCl (3 N) and stirred for 18 h at RT. This solution was concentrated in vacuo to give a white solid. This solid was triturated and dried to give 29 as a white foam (0.144 g): $^1$H NMR (DMSO-d$_6$) δ 9.0 (m, 1H), 8.6 (m, 1H), 8.3 (m, 1H), 7.2 (m, 5H), 4.48 (s, 2H), 4.2

(m, 2H), 3.7 (m, 1H), 3.4 (m, 1H), 3.2 (d, 3H), 2.7 (d, 3H), 2.2 (m, 3H), 1.7 (m, 3H), 1.0–1.6 (m, 10H); MS m/e 470 (MH⁺).

Example 30
N-3-(4-Piperidinepropionyl)-R-(−)nipecotyl-[(S)-2-(2-phenethylamino)carbonylamino-3-amino]propionic acid.HCO₂H (30)

Compound 30, prepared by reacting 2-phenethylisocyanate (4.1 mmol mmol) with AH2 (4.1 mmol) as shown in Example 22, was isolated as a tan foam (0.41 g): mp 65–72° C.; MS m/e 502 (MH⁺). Anal. calcd. for $C_{26}H_{39}N_5O_5 \cdot 1.2HCO_2H \cdot 1.0$ H₂O (574.87): C, 56.83; H, 7.61; N, 12.18 Found: C, 57.12; H, 7.80; N, 11.85.

6-Methyl-3-pyridine-carboxaldehyde (AK2)

Aldehyde precursor AK2 was prepared in two steps using standard conditions. AK1 (0.066 mol) was dissolved in THF (100 mL), cooled (−78° C.), treated with LiAlH₄ (0.066 mol), and stirred for 4 h. The reaction was quenched with sat'd NH₄Cl, warmed, filtered with CHCl₃ washes (250 mL), and the layers separated. The organic layer was dried and evaporated to give a clear oil (0.054 mol). The oil was dissolved in DCM (200 mL), treated with MnO₂ (70 g), and heated at reflux for 6 h. The mixture was cooled, filtered, and the solvent evaporated to give AK2 (0.052 mol) as a brown oil.

Example 31
N-3-(4-Piperidinepropionyl)-R-(−)nipecotyl-[(S)-3-amino-3-(6-methyl-3-pyridyl)]propionic acid.2HCl (31)

Compound 31, prepared as described in Example 16 starting with Boc-R-nipecotic acid (6.9 mmol) and methyl (S)-3-amino-3-(6-methyl-3-pyridyl)propionate (see examples AK5, AG5; 6.9 mmol). Compound 31 was isolated as a white foam (1.20 g): mp 99–105° C.; MS m/e 431 (MH⁺). Anal. calcd. for $C_{23}H_{34}N_4O_4 \cdot 2.24$ HCl·1.0H₂O·0.24 Acetonitrile (534.33): C, 51.70; H, 7.35; N, 11.11; Cl, 14.82. Found: C, 51.32; H, 7.45; N, 11.23; Cl, 14.42.

Example 32
N-3-(4-Piperidinepropionyl)-R-(−)nipecotyl-[(S)-3-amino-3-(5-bromo-3-pyridyl)]propionic acid.2HCl (32)

Compound 32, prepared as described in Example 16 starting with Boc-R-nipecotic acid (4.8 mmol) and methyl 3-S-amino-3-(5-bromo-3-pyridyl)propionate (see examples AK5, AG5; 4.8 mmol), was isolated as a white foam (1.24 g): mp 98–101° C.; MS m/e 496 (MH⁺). Anal. calcd. for $C_{22}H_{31}BrN_4O_4 \cdot 2.2$ HCl·1.0H₂O (593.67): C, 44.51; H, 5.98; N, 9.44; Cl, 13.14. Found: C, 44.17; H, 6.37; N, 9.81; Cl, 13.10.

Example 33
N-3-(4-Formamidinopiperidinepropionyl)-R-(−)nipecotyl-[(S)-3-amino-3-(3-pyridyl)]propionic acid.2HCl (33)

Formamidine 33 was prepared according to the procedure of M. K. Scott (J. Med. Chem. 1983, 26, 534) as shown in Scheme AL. Intermediate AL1 (see Example 21; 2.3 mmol) was dissolved in EtOH (20 mL), treated with ethyl formimidate.HCl (3.7 mmol), stirred for 22 h, and filtered. The filtrate was treated with Et₂O (40 mL), cooled in an ice bath, and filtered to give glassy AL2. AL2 was dissolved in aq. HCl (4N, 15 mL), stirred for 28 h, and evaporated to give 33 as a white foam (0.75 g): mp 49–55° C. ¹H NMR (DMSO-d₆) δ 9.35 (s, 1H), 9.1 (m, 2H), 8.8 (m, 2H), 8.70 (d, 1H), 8.5 (m, 1H), 7.8 (m, 2H), 5.2 (dd, 1H), 4.2 (m, 1H), 3.8 (m, 2H), 3.2 (m, 2H), 2.8 (m, 2H), 2.6 (m, 1H), 2.3 (m, 2H), 1.8 (m, 3H), 1.0–1.7 (m, 12H); MS m/e 444 (MH⁺).

We claim:

1. A compound of the formula:

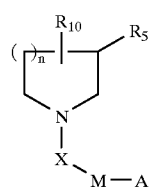

(I)

wherein:

$R_{10}$ is H or $C(O)N(R^1)YZ$, wherein $R^1$ is H; Y is $(CH_2)_p$, $(CH_2)_qCHR^3$ or $CH(R^3)(CH_2)_q$, wherein $R^3$ is aryl, aralkyl or heteroaryl, q is 1–3 and p is 2 or 3;

Z is $CO_2H$, $CO_2$-alkyl, or 5-tetrazole;

X is C(O);

M is $(CH_2)_m$ or piperidin-1-yl, wherein m is 2;

n is 2;

$R_5$ is H;

A is selected from any of piperidin-2-yl, piperidin-3-yl, piperidin-4-yl or

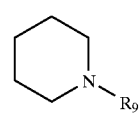

wherein $R_9$ is H enantiomers and the pharmaceutically acceptable salts thereof alkyl, CH(NH), CMe(NH) or acyl.

2. The compound of claim 1 selected from the group consisting of:

N-3-(4-Piperidinepropionyl)-nipecotyl-(3-amino-3-phenyl) propionic acid,

N-3-(4-Piperidinepropionyl)-isonipecotyl-[3-amino-3-(4-carboxyphenyl)]propionic acid, N-3-(4-Piperidinepropionyl)-nipecotyl-5H-(2-aminoethyl) tetrazole, N-3-(4-Piperidinepropionyl)-R-(−)-nipecotyl-[(S)-3-amino-3-(3,4-methylenedioxyphenyl)]propionic acid, N-3-(4-Piperidinepropionyl)-R-(−)-nipecotyl-[(S)-3-amino-3-(3-quinolinyl)]propionic acid, N-3-(4-Piperidinepropyl)-nipecotyl-[(S)-3-amino-3-(3,4-methylenedioxyphenyl)]propionic acid, N-3-(4-Piperidinepropionyl)-R-(−)-nipecotyl-[(S)-3-amino-3-(3-pyridyl)]propionic acid, N-[(4,4'-Bipiperidin-1-yl-)carbonyl]-R-(−)-nipecotyl-[(S)-3-amino-3-(3-pyridyl)]propionic acid, N-3-(4-Piperidinepropionyl)-R-(−)-nipecotyl-[(S)-3-amino-3-(6-methyl-3-pyridyl)]propionic acid, N-3-(4-Piperidinepropionyl)-R-(−)-nipecotyl-[(S)-3-amino-3-(5-bromo-3-pyridyl)]propionic acid, and N-3-(4-Formamidinopiperidinepropionyl)-R-(−)-nipecotyl-[(S)-3-amino-3-(3-pyridyl)]propionic acid.

* * * * *